(12) United States Patent
Davies

(10) Patent No.: US 6,410,746 B1
(45) Date of Patent: Jun. 25, 2002

(54) METAL CATALTSTS AND METHODS FOR MAKING AND USING SAME

(75) Inventor: Huw M. L. Davies, Clarence Center, NY (US)

(73) Assignee: Research Foundation of State University of New York, The, Amherst, NY (US)

(*) Notice: Subject to any disclaimer, the term of this patent is extended or adjusted under 35 U.S.C. 154(b) by 0 days.

(21) Appl. No.: 09/521,375

(22) Filed: Mar. 8, 2000

Related U.S. Application Data

(60) Provisional application No. 60/131,262, filed on Apr. 27, 1999.

(51) Int. Cl.$^7$ .............................. C07F 15/00; C07F 7/02; C07F 9/02; B01J 31/00
(52) U.S. Cl. ...................... 548/403; 556/136; 556/466; 564/336; 564/340; 568/14; 568/15; 568/17; 502/166
(58) Field of Search ................................. 556/136, 466; 548/403; 502/166; 564/336, 340; 568/14, 15, 17

(56) References Cited

U.S. PATENT DOCUMENTS

| | | | |
|---|---|---|---|
| 2,507,631 A | 5/1950 | Hartmann et al. | 260/294 |
| 2,957,880 A | 10/1960 | Rometsch et al. | 260/294 |
| 4,133,881 A | 1/1979 | Cale, Jr. et al. | 424/244 |
| 4,238,488 A | 12/1980 | Howe et al. | 424/248.55 |
| 4,866,048 A | 9/1989 | Calverley et al. | 514/167 |
| 5,036,053 A | 7/1991 | Himmelsbach et al. | 514/19 |
| 5,296,595 A | 3/1994 | Doyle | 540/200 |
| 5,401,732 A | 3/1995 | Calverley et al. | 514/167 |
| 5,665,890 A | 9/1997 | Jacobsen et al. | 549/230 |

FOREIGN PATENT DOCUMENTS

GB    2 260 903 A    5/1993

OTHER PUBLICATIONS

Deutsch et al., "Synthesis and Pharmacology of Potential Cocaine Antagonists. 2. Structure—Activity Relationship Studies of Aromatic Ring–Substituted Methylphenidate Analogs," *J. Med. Chem.*, 39:1201–1209 (1996).

Doyle et al., "Chiral Catalysts for Enantioselective Intermolecular Cyclopropanation Reactions With Methyl Phenyldiazoacetate. Origin of the Solvent Effect in Reactions Catalyzed by Homochiral Dirhodium(II) Prolinates," *Tetrahedron Letters*, 37(24):4129–4132 (1996).

Davies et al., "Asymmetric Intermolecular Carbenoid C–H Insertions Catalyzed by Rhodium(II) (S)–N–(p–Dodecylphenyl)sulfonylprolinate," *J. Chem. Soc.*, 119:9075–9076 (1997).

Davies, "Asymmetric Synthesis Using Rhodium–Stabilized Vinylcarbenoid Intermediates," *Aldrichimica Acta*, 30(4):107–114 (1997).

Davies et al., "Synthesis and Evaluation of a Novel Dirhodium Tetraprolinate Catalyst Containing Bridging Prolinate," *Tetrahedron Letters*, 38(24):4203–4206 (1997).

Axten et al., "A Stereoselective Synthesis of dl–threo–Methylphenidate: Preparation and Biological Evaluation of Novel Analgoues," *J. Org. Chem.*, 63:9628–9629 (1998).

Davies et al., "Effect of Carbenoid Structure on the Reactivity of Rhodium Stabilized Carbenoids," *Tetrahedron Letters*, 39:4417–4420 (1998).

Davies, "Rhodium–Stabilized Vinylcarbenoid Intermediates in Organic Synthesis," *Current Organic Chemistry*, 2:463–488 (1998).

Stinson, "Counting on Chiral Drugs," *Chemical & Engineering News*, pp. 83ff (Sep. 21, 1998).

Thai et al., "Asymmetric Synthesis and Pharmacology of Methylphenidate and Its Para–Substituted Derivatives," *J. Med. Chem.*, 41:591–601 (1998).

Axten et al., "Enantioselective Synthesis of D–threo–Methylphenidate," *J. Am. Chem Soc.*, 121(27):6511–6512 (1999).

Davies et al., "Catalytic Asymmetric Synthesis of Diarylacetates and 4,4–Diarylbutanoates. A Formal Asymmetric Synthesis of (+)–Sertraline," *Organic Letters*, 1(2):233–236 (1999).

(List continued on next page.)

*Primary Examiner*—Porfirio Nazario-Gonzalez
(74) *Attorney, Agent, or Firm*—Braman & Rogalskyj, LLP

(57) ABSTRACT

Compounds having the formula:

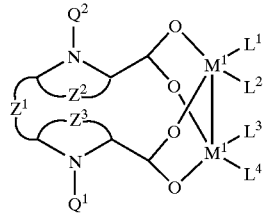

are disclosed. $M^1$ and $M^2$ are the same or different and are transition metal atoms or ions; $Z^2$ and $Z^3$, independently, are the atoms necessary to complete a 3–12 membered heterocyclic ring; $Z^1$ is an alkylene or arylene group; $Q^1$ and $Q^2$ are the same or different and are electron withdrawing groups; $L^1$ and $L^3$, taken together, represent —O—$CR^{13}$—O—; $L^2$ and $L^4$, taken together, represent —O—$CR^{14}$—O—; and $R^{13}$ and $R^{14}$ are the same or different and are selected from the group consisting of alkyl groups and aryl groups or $R^{13}$ and $R^{14}$ represent alkylene or arylene groups that are directly or indirectly bonded to one another. Methods for making such compounds are also disclosed, as are intermediates which can be used in their preparation. Also disclosed are methods for carrying out C—H insertion reactions using bis-transition metal catalysts, such as the above compounds. Procedures for preparing d-threo methylphenidate, tolterodine, CDP-840, nominfensine, and sertraline, are described.

34 Claims, No Drawings

OTHER PUBLICATIONS

Davies et al., "Catalytic Asymmetric Synthesis of Syn–Aldol Products from Intermolecular C–H Intersections Between Allyl Silyl Ethers and Methyl Aryldiazoacetates," *Organic Letters*, 1(3):383–385 (1999).

Davies, "Dirhodium Tetra(N–arylsulfonylprolinates) as Chiral Catalysts For Asymmetric Transformations of Vinyl–and Aryldiazoacetates," *Eur. J. Org. Chem.*, 2459–2469 (1999).

Davies et al., "Highly Regio–, Diastereo–and Enantioselective C–H Insertions of Methyl Aryldiazoacetates into Cyclic N–Boc–Protected Amines. Asymmetric Synthesis of Novel C2–Symmetric Amines and threo–Methylphenidate," *J. Am. Cell Soc.*, 121(27):6509–6510 (1999).

Davies et al., "Novel Dirhodium Tetraprolinate Catalysts Containing Bridging Prolinate Ligands for Asymmetric Carbenoid Reactions," *Tetrahedron Letters*, 40:5287–5290 (1999).

Deutsch et al., "Synthesis and Pharmacology of Site–Specific Cocaine Abuse Treatment Agents: 2–(Aminomethyl)–3–phenylbicyclo[2.2.2]–and –[2.2.1.]alkane Dopamine Uptake Inhibitors," *J. Med. Chem.*, 42:882–895 (1999).

Matsumura et al., "A Convenient Method for Synthesis of Enantiomerically Enriched Methylphenidate from N–Methoxycarbonylpiperidine," *Organic Letters*, 1(2):175–178 (1999).

Prashad et al., "Enantioselective Synthesis of (2S, 2'R)–erythro–methylphenidate," *Tetrahedron: Asymmetry*, 10:3479–3482 (1999).

Prashad et al., "The First Enantioselective Synthesis of (2R,2'R)–threo–(±)–Methylphenidate Hydrochloride," *J. Org. Chem.*, 64:1750–753 (1999).

Davies et al., "Enantioselective Synthesis of Functionalized Tropanes by Rhodium (II) Carboxylate–Catalyzed Decomposition of Vinyldiazomethanes in the Presence of Pyrroles," *J. Org. Chem.*, 62:1095–1105 (1997).

Deutsch et al., "Synthesis and Pharmacology of Site–Specific Cocaine Abuse Treatment Agents: The Role of the Phenyl Group in Highly Modified Methylphenidate Analogs as Dopamine Uptake Inhibitors," *Med. Chem. Res.*, 9(4):213–222 (1999).

Davies et al., "Stereoselectivity of Methyl Aryldiazoacetate Cyclopropanations of 1,1–Diarylethylene. Asymmetric Synthesis of a Cyclopropyl Analogue of Tamoxifen," *Organic Letters*, 2(6):823–826 (2000).

Davies et al., "Catalytic Asymmetric Synthesis of Diarylacetates and 4,4–Diarylbutanoates. A Formal Asymmetric Synthesis of (+)–Setraline," *Organic Letters*, 2(3):417 (2000).

METAL CATALTSTS AND METHODS FOR MAKING AND USING SAME

The present application claims the benefit of U.S. Provisional Patent Application Serial No. 60/131,262, filed Apr. 27, 1999.

The present invention was made with the support of the National Science Foundation Contract No. CHE 9726124 and National Institutes of Health Contract Nos. DA06301 and DA05886. The Federal Government may have certain rights in this invention.

FIELD OF THE INVENTION

The present invention relates to metal catalysts and, more particularly, to bis transition metal catalysts and to methods for making and using same.

BACKGROUND OF THE INVENTION

Catalysts

In recent years, it has become widely recognized that ligands having $C_2$ symmetry can be used with great effect in the design of catalysts for asymmetric synthesis. Several reviews have addressed the use of such catalysts in asymmetric carbenoid reactions. These include: Singh et al., "Catalytic Enantioselective Cyclopropanation of Olefins Using Carbenoid Chemistry," *Synthesis*, 1997:137–149 and Doyle, Chiral catalysts for Enantioselective Carbenoid Cyclopropanation Reactions," *Recl. Trav. Chim. Pays-Bas*, 110:305–316 (1991). The use of these catalysts in asymmetric transformations has also been reported in Pfaltz, "Chiral Semicorrins and Related Nitrogen Heterocycles as Ligands in Asymmetric Catalysts," *Acc. Chem. Res.*, 26:339–345 (1993); Noyori, *Asymmetric Catalysis in Organic Synthesis*, New York: John Wiley & Sons, Inc., pp. 16–95 (1994); Evans et al., "Bis(oxazoline)-copper Complexes as Chiral Catalysts for the Asymmetric Aziridination of Olefins," *J. Am. Chem. Soc.*, 115:3328–3329 (1993); Li et al., "Asymmetric Alkene Aziridination With Readily Available Chiral Diimine-based Catalysts," *J. Am. Chem. Soc.*, 115:5326–5327 (1993); Nishikori et al., "Catalytic and Highly Enantioselective Aziridination of Styrene Derivatives," *Tetrahedron Lett.*, 37:9245–9248 (1996); Nicholas et al., "On the Mechanism of Alyllic Amination Catalyzed by Iron Salts," *J. Am. Chem. Soc.*, 119:3302–3310 (1997); Johnson et al., "Catalytic Asymmetric Epoxidation of Allylic Alcohols," in Ojima, ed., *Catalytic Asymmetric Synthesis*, New York: VCH Publishers, Inc., pp. 103–158 (1993); and Jacobsen, "Asymmetric Catalytic Epoxidation of Unfunctionalized Olefins," in Ojima, ed., *Catalytic Asymmetric Synthesis*, New York: VCH Publishers, Inc., pp. 159–202 (1993). The $C_2$ symmetry of a complex cuts in half the number of possible arrangements that are available for the reacting substrate or substrates. Consequently, it becomes much easier to design a catalyst with well-defined chiral influence to effect high asymmetric induction of the reaction in question. A natural extension for chiral catalyst design would be to move from complexes having $C_2$ symmetry to complexes having $D_2$ symmetry. Catalysts having $D_2$ symmetry would cut to a quarter the number of possible arrangements that re available for the reacting substrate or substrates and, thus, would have the potential of being very reliable chiral catalysts.

Even though the concept of using catalysts having $D_2$ symmetry is a very attractive proposition, the practical outcome of trying to delvelop such catalysts has not had much success. The general strategy, such as that described in Maxwell et al., "Shape-selective and Asymmetric Cyclopropanation of Alkenes Catalyzed by Rhodium Porphyrins," *Organometallics*, 11:645–652 (1992) ("Maxwell"), Morice et al., "Oxidation and Chiral Recognition of Amino Esters by Dioxoruthenium(VI) Porphyrins: Synthesis of a New Imino Ester Ru(II) Complexes," *Tetrahedron Lett.*, 37:6701–6704 (1996), and Halterman et al., "Synthesis of $D_2$-symmetric Benzaldehydes and Achiral Arylsipyrromethanes," *Tetrahedron Lett.*, 37:6291–6294 (1996), has been to develop very elaborate $D_2$ ligands built around a porphyrin core. However, the synthetic procedures for these ligands are long and give poor yields, and the resulting chiral catalysts perform only with moderate asymmetric induction. Maxwell suggests that one problem with these porphyrin complexes is that the chiral influence is too far removed from the metal center to be very effective in asymmetric induction.

In view of the unrealized promise of catalysts having $D_2$ symmetry, there is a need for catalysts having $D_2$ symmetry which are easily to produce and which have high asymmetric inductive effects. The present invention, in part, is directed to meeting this need.

Synthesis of Gem-Diarylalkyl Derivatives

The gem-diarylalkyl group is present in a number of important pharmaceuticals, such as tolterodine, CDP-840, and nomifensine, and sertraline. Consequently, a number of reports have recently appeared describing methods for the asymmetric synthesis of gem-diarylalkyl derivatives. These include: Frey et al., *J. Org. Chem.*, 63:3120–3124 (1998) ("Frey"); Andersson et al., *J. Org. Chem.*, 63:8067–8070 (1998) ("Andersson"); Houpis et al., *Tetrahedron Lett.*, 38:7131–7134 (1997) ("Houpis"); Christenson et al., *Tetrahedron*, 47:4739–4752 (1991) ("Christenson"); Alexakis et al., *Tetrahedron Lett.*, 29:4411–4414 (1988) ("Alexakis"); and Corey et al., *Tetrahedron Lett.*, 35:5373–5376 (1994) ("Corey"). Particularly effective have been the asymmetric conjugate addition of organometallic reagents to cinnamates, decribed in Frey, Andersson, Houpis, Christenson, and Alexakis, and the aryl cuprate addition to enantiomerically pure dimethyl 2-phenylcyclopropane-1,1-dicarboxylate, described in Corey. However, these reaction schemes involve multiple steps with poor overall yields and inconsistent chiral purity.

Accordingly, a need continues to exist for methods for preparing asymmetric gem-diarylalkyl derivatives. The present invention, in part, is directed to meeting this need.

Formation of Carbon-Carbon Bonds

The aldol reaction is a central transformation in organic synthesis. See, for example, Heathcock in Morrison, ed., *Asymmetric Synthesis*, San Diego: Academic Press, Vol. 3, Chapter 2 (1984) ("Heathcock"). Not only is the reaction a powerful carbon-carbon bond forming process, but, also, Heathcock reports that the reaction can be made highly diastereoselective by using enolates of defined geometry. Furthermore, high enantioselectivity can be achieved by using chiral auxiliaries (Heathcock) or by using chiral catalysts. The use of chiral catalysts in enantioselective aldol reactions has been recently reviewed in Nelson, "Catalyzed Enantioselective Aldol Additions of Latent Enolate Equivalents," *Tetrahedron-Asymmetry*, 9:357–389 (1998). Of particular interest are aldol reactions between enolates of arylacetates and aldehydes. For example, Evans et al., "C-2-symmetric Copper(II) Complexes as Chiral Lewis Acids. Scope and Mechanism of the Catalytic Enantioselective Aldol Additions of Enolsilanes to Pyruvate Salts," *J. Am. Chem. Soc.*, 121:669–699 (1999), recently reported a reaction between a silylketene acetal of phenylacetate and benzyloxyacetaldehyde using a Cu(II) bisoxazoline complex. The reaction resulted in low enantioselectivity (about 9%) and no diastereoselectivity. However, better asymmetric induction has been achieved in such aldol reactions by using chiral enolates (Lutzen et al., "D-xylose Derived Oxazolidin-2-ones as Chiral Auxiliaries in Stereoselective Aldol Reactions," *Tetrahedron-Asymmetry.* 8:1193–1206 (1997)). However, processes of this type occurring in high yields and with good diastereoselectivity and enantioselectivity has not been reported.

Accordingly, a need continues to exist for methods for forming carbon-carbon bonds with good diastereoselectivity and enantioselectivity. The present invention, in part, is directed to meeting this need.

RITALIN™ and its Congeners

Attention Deficit Disorder ("ADD") is the most commonly diagnosed illness in children. Symptoms of ADD include distractibility and impulsivity. A related disorder, termed Attention Deficit Hyperactivity Disorder ("ADHD"), is further characterized by increased symptoms of hyperactivity in patients. Racemic methylphenidate (e.g., RITALIN™) is a mild central nervous system stimulant, with pharmacological activity qualitatively similar to amphetamines, and has been the drug of choice for symptomatic treatment of ADD in children. Current administration of racemic methylphenidate, however, results in notable side effects, such as anorexia, weight loss, insomnia, dizziness, and dysphoria. Additionally, racemic methylphenidate, which is a Schedule II controlled substance, produces a euphoric effect when administered intravenously or through inhalation and, thus, carries a high potential for substance abuse in patients.

At least 70% individuals who are infected with the Human Immunodeficiency Virus ("HIV") who have developed Acquired Immunodeficiency Syndrome ("AIDS") eventually manifest cognitive defects, and many display signs and symptoms of dementia. Complaints of forgetfulness, loss of concentration, fatigue, depression, loss of attentiveness, mood swings, personality change, and thought disturbance are common in patients with HIV disease. Racemic methylphenidate has been used to treat cognitive decline in AIDS patients. As described above, racemic methylphenidate, which is a Schedule II controlled substance, produces a euphoric effect when administered intravenously or through inhalation, and thus carries a high potential for drug abuse in AIDS patients.

Glutathione is an important antioxidative agent that protects the body against electrophilic reactive compounds and intracellular oxidants. It has been postulated that HIV-AIDS patients suffer from drug hypersensitivity due to drug overload and an acquired glutathione deficiency. Patients with HIV infection have demonstrated a reduced concentration of glutathione in plasma, cells, and broncho-alveolar lavage fluid. Clinical data suggest that HIV-seropositive individuals display adverse reactions to the simultaneous administration of several otherwise therapeutic drugs. It is therefore desirable to provide for the administration of methylphenidate in reduced dosages among patients with drug hypersensitivity due to HIV infection.

Methylphenidate possesses two centers of chirality and thus can exist as four separate stereoisomers. Diastereomers are known in the art to possess differing physical properties, such as melting point and boiling point. For example, while the threo-racemate of methylphenidate produces the desired effect on the cental nervous system, the erythro-racemate contributes to hypertensive side-effects and exhibits lethality in rats.

Additional studies in animals, children and adults have demonstrated pharmacological activity in the d-threo isomer of methylphenidate (2R:2'R). Although the role of the l-threo isomer in toxicity or adverse side effects has not been thoroughly examined, the potential for isomer ballast in methylphenidate is of concern for many patients, particularly those drug hypersensitive patients described above.

Although l-threo-methylphenidate is rapidly and stereoselectively metabolized upon oral administration, intravenous administration or inhalation results in high l-threo-methylphenidate serum levels. Intravenous administration and inhalation are the methods of-choice by drug abusers of current methylphenidate formulations, and it has been postulated that the euphoric effect produced by current formulations of methylphenidate is due to the action of the l-threo-methylphenidate.

Accordingly, it has been suggested that the use of the d-threo isomer (2R:2'R) of methylphenidate which is substantially free of the l-threo isomer produces high methylphenidate activity levels and simultaneously reduces methylphenidate's euphoric effect and the potential for abuse among patients.

Methods for synthesizing d-threo methylphenidate have been reported. However, these methods involve long, complicated syntheses, have poor overall yields, and require at least some separation of mixtures of enantiomers and/or diastereomers.

In view of the advantages of pure d-threo methylphenidate and the deficiency in the art of methods for making this compound and its congeners, a need exists for an improved synthetic method for making pure d-threo methylphenidate and its congeners. The present invention, in part, is directed to meeting this need.

SUMMARY OF THE INVENTION

The present invention relates to a compound having the formula:

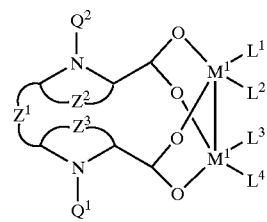

wherein $M^1$ and $M^2$ are the same or different and are transition metal atoms or ions; $Z^2$ and $Z^3$, independently, are the atoms necessary to complete a 3–12 membered heterocyclic ring; $Z^1$ is an alkylene or arylene group; $Q^1$ and $Q^2$ are the same or different and are electron withdrawing groups; $L^1$ and $L^3$, taken together, represent —O—$CR^{13}$—O—; $L^2$ and $L^4$, taken together, represent —O—$CR^{14}$—O—; and $R^{13}$ and $R^{14}$ are the same or different and are selected from the group consisting of alkyl groups and aryl groups or $R^{13}$ and $R^{14}$ represent alkylene or arylene groups that are directly or indirectly bonded to one another.

The present invention also relates to a compound which includes a first metal atom and a second metal atom that are bonded to one another along an axis and two carboxylate ligands. Each of the two carboxylate ligands includes two carboxylate groups bonded to each other via a moiety having the formula:

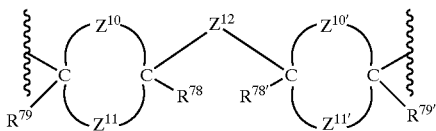

where $Z^{10}$ and $Z^{11}$, together with the atoms to which they are bonded form a 3–12 membered ring; $Z^{10'}$ and $Z^{11'}$, together with the atoms to which they are bonded form a 3–12 membered ring; and $R^{78}$, $R^{78'}$, $R^{79}$, and $R^{79'}$ are independently selected from the group consisting of H, an alkyl group, and an aryl group. $Z^{12}$ is an alkylene or arylene group. Each of the two carboxylate groups includes a first carboxylate oxygen atom ("$O^1$"), a second carboxylate oxygen atom ("$O^2$"), and a carbon ("C") to which the $O^1$ and the $O^2$ are bonded thereby forming two $O^1$—C—$O^2$ moieties, and each $O^1$—C—$O^2$ moiety defines a plane which is substantially parallel to the axis. $O^1$ of each of the two carboxylate groups of each of the two carboxylate ligands is bonded to the first metal atom, and $O^2$ of each of the two carboxylate groups of each of the two carboxylate ligands is bonded to the second metal atom. Each of the two carboxylate ligands further includes at least two chiral centers, and the compound has $D_2$ symmetry.

The present invention also relates to a method for making a compound having the formula:

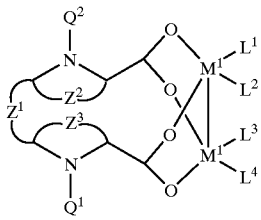

wherein $M^1$ and $M^2$ are the same or different and are transition metal atoms or ions; $Z^2$ and $Z^3$, independently, are the atoms necessary to complete a 3–12 membered heterocyclic ring; $Z^1$ is an alkylene or arylene group; $Q^1$ and $Q^2$ are the same or different and are electron withdrawing groups; $L^1$ and $L^3$, taken together, represent —O—CHR$^{13}$—O—; $L^2$ and $L^4$, taken together, represent —O—CHR$^{14}$—O—; and $R^{13}$ and $R^{14}$ are the same or different and are selected from the group consisting of alkyl groups and aryl groups or $R^{13}$ and $R^{14}$ represent alkylene or arylene groups that are directly or indirectly bonded to one another. The method includes providing a ligand having the formula:

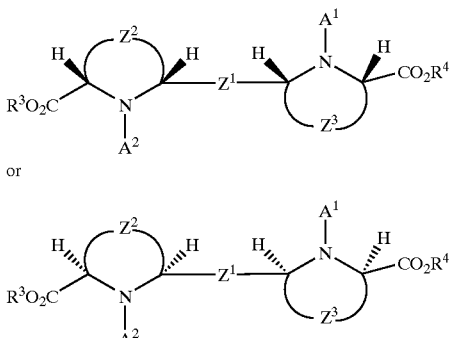

or a mixture thereof, wherein each of $A^1$ and $A^2$ is independently selected from the group consisting of a hydrogen atom and an electron withdrawing group and wherein each of $R^3$ and $R^4$ is independently selected from the group consisting of H, alkyl, and aryl. The method further includes converting the ligand with a bis-metal salt under conditions effective to produce the compound.

The present invention also relates to compounds having one of the following formulae:

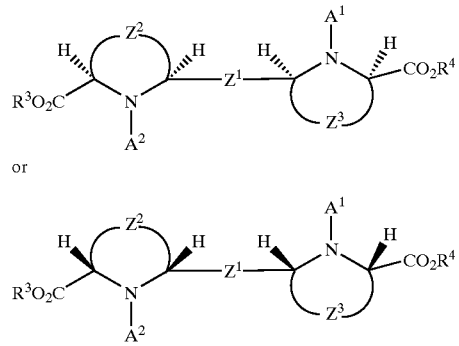

wherein $Z^2$ and $Z^3$, independently, are the atoms necessary to complete a 3–12 membered heterocyclic ring; $Z^1$ is an alkylene or arylene group; $A^1$ and $A^2$ are independently selected from the group consisting of a hydrogen atom and an electron withdrawing group; and each each of $R^3$ and $R^4$ is independently selected from the group consisting of H, alkyl, and aryl.

The present invention also relates to a method for preparing an N-substituted compound having the formula:

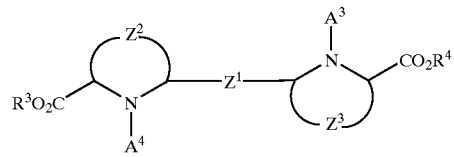

wherein $Z^2$ and $Z^3$, independently, are the atoms necessary to complete a 3–12 membered heterocyclic ring; $Z^1$ is an alkylene or arylene group; $A^3$ and $A^4$ are the same or different and are electron withdrawing groups having the formulae —C(O)R$^2$, —SO$_2$R$^2$, or —P(O)R$^2$R$^{2'}$; each of $R^1$, $R^{1'}$, $R^2$, and $R^{2'}$ is an alkyl group, an aryl group, or an alkoxy group; and each of $R^3$ and $R^4$ is independently selected from the group consisting of H, alkyl, and aryl. The method includes providing an N-unsubstituted compound having the formula:

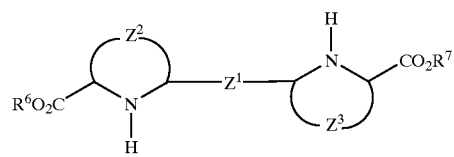

wherein each of $R^6$ and $R^7$ is independently selected from an alkyl group or an aryl group. The method further includes converting the N-unsubstituted compound to the N-substituted compound with an acylating agent, a sulfonylating agent, or a phosphonylating agent.

The present invention also relates to a method for preparing an N-unsubstituted compound having the formula:

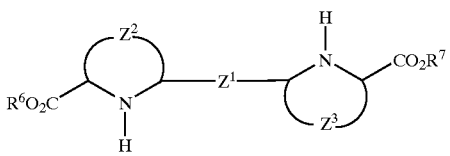

wherein $Z^2$ and $Z^3$, independently, are the atoms necessary to complete a 3–12 membered heterocyclic ring; $Z^1$ is an alkylene or arylene group; and $R^6$ and $R^7$ are independently selected from an alkyl group or an aryl group. The method includes providing an unsaturated heterocyclic compound having the formula:

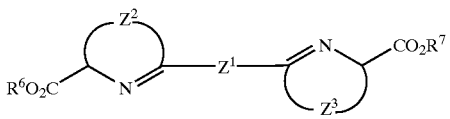

and converting the unsaturated heterocyclic compound to the N-unsubstituted compound using hydrogenation.

The present invention, in still another embodiment thereof, relates to a compound having one of the following formulae:

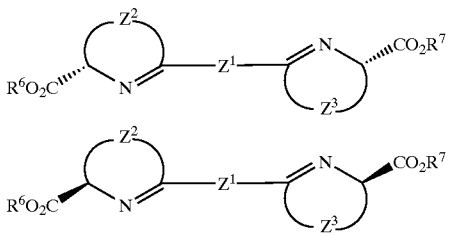

wherein $Z^2$ and $Z^3$, independently, are the atoms necessary to complete a 3–12 membered heterocyclic ring; $Z^1$ is an alkylene or arylene group; and $R^6$ and $R^7$ are independently selected from an alkyl group or an aryl group.

The present invention also relates to a method for preparing an unsaturated heterocyclic compound having the formula:

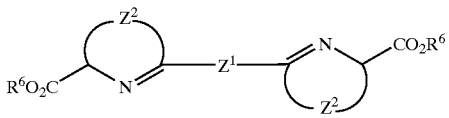

wherein $Z^2$ represents the atoms necessary to complete a 3–12 membered heterocyclic ring; $Z^1$ is an alkylene or arylene group; and $R^6$ is selected from an alkyl group or an aryl group. The method includes providing a cyclic ketone having the formula:

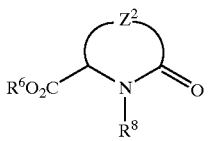

wherein $R^8$ is an amine-protecting group. The method further includes converting the cyclic ketone to the N-unsaturated heterocyclic compound with a bis-lithium compound having the forrmula $Z^1Li_2$.

The present invention further relates to a method of producing a compound having the formula:

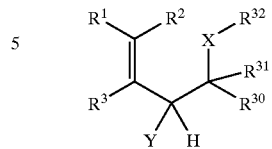

where $R^1$, $R^2$, and $R^3$ are independently selected from H, alkyl, aryl, or vinyl or where $R^1$ and $R^3$, together with the atoms to which they are bonded, form a 5–12 membered ring; Y is an electron withdrawing group; X is $CH_2$, O, or $NR^{11}$; $R^{11}$ is H, an alkyl group, an aryl group, an acyl group, an alkoxycarbonyl group, or a silyl group having the formula —$SiR^{33}R^{34}R^{35}$; each of $R^{30}$ and $R^{31}$ is independently selected from the group consisting of H, alkyl, aryl, and vinyl; $R^{32}$ is an alkyl group, an aryl group, an acyl group, an alkoxycarbonyl group, or a silyl group having the formula —$SiR^{36}R^{37}R^{38}$; or $R^{31}$ and $R^{32}$, together with the atoms to which they are bonded, form a 5–12 membered ring; $R^{33}$, $R^{34}$, $R^{35}$, $R^{36}$, $R^{37}$, and $R^{38}$ are independently selected from an alkyl group and an aryl group; provided that when each of $R^{30}$ and $R^{31}$ is H, X is not $CH_2$. The method includes providing a diazo compound having the formula:

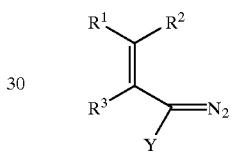

and converting the diazo compound with a compound having the formula:

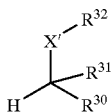

in the presence of a bis-transition metal catalyst, under conditions effective to produce the compound. In the immediately preceding formula, X' is $CH_2$, O, or $NR^{11'}$ and $R^{11'}$ is an alkyl group, an aryl group, an acyl group, an alkoxycarbonyl group, or a silyl group. When when X is O or $CH_2$, when $R^1$ and $R^3$, together with the atoms to which they are bonded, form a 5–12 membered ring, and when $R^{31}$ and $R^{32}$, together with the atoms to which they are bonded, form a 5–12 membered ring, conversion of the diazo compound is carried out substantially in the absence of oxygen.

In yet another embodiment, the present invention relates to a method for producing a compound having the formula:

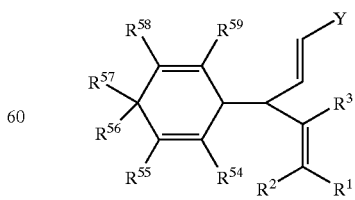

wherein $R^1$, $R^2$, and $R^3$ are independently selected from H, an alkyl group, an aryl group, or a vinyl group or where $R^1$ and $R^3$, together with the atoms to which they are bonded, form a 5–12 membered ring; Y is an electron withdrawing group; and $R^{54}$, $R^{55}$, $R^{56}$, $R^{57}$, $R^{58}$, and $R^{59}$ are independently selected from the group consisting of H, alkyl, aryl, halogen, and alkoxy. The method includes providing a 1,3-cyclohexadiene having the formula:

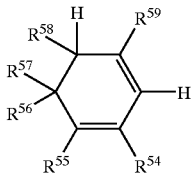

The method further includes converting the 1,3-cyclohexadiene with a diazo compound having the formula:

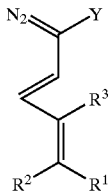

in the presence of a bis-transition metal catalyst and under conditions effective to produce the compound.

The present invention also relates to a compound having the formula:

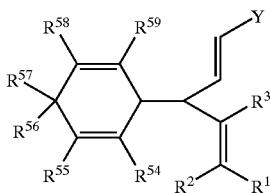

$R^1$, $R^2$, and $R^3$ are independently selected from H, an alkyl group, an aryl group, or a vinyl group, or $R^1$ and $R^3$, together with the atoms to which they are bonded, form a 5–12 membered ring. Y is an electron withdrawing group. $R^{54}$, $R^{55}$, $R^{56}$, $R^{57}$, $R^{58}$, and $R^{59}$ are independently selected from the group consisting of H, alkyl, aryl, halogen, and alkoxy.

In still another embodiment, the present invention relates to a method for making a compound having the formula:

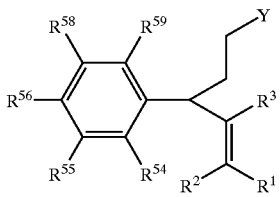

in which $R^1$, $R^2$, and $R^3$ are independently selected from H, an alkyl group, an aryl group, or a vinyl group or where $R^1$ and $R^3$, together with the atoms to which they are bonded, form a 5–12 membered ring; Y is an electron withdrawing group; and $R^{54}$, $R^{55}$, $R^{56}$, $R^{58}$, and $R^{59}$ are independently selected from the group consisting of H, alkyl, aryl, halogen, and alkoxy. The method includes providing a cyclohexadiene derivative having the formula:

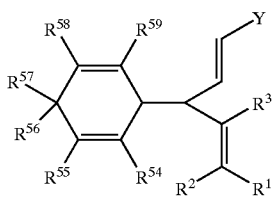

wherein $R^{57}$ is H. The method further includes converting the cyclohexadiene derivative with hydrogenating and oxidizing agents under conditions effective to form the compound.

The present invention also relates to a method for preparing a compound having the formula:

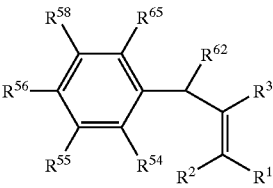

$R^1$, $R^2$, and $R^3$ are independently selected from H, an alkyl group, an aryl group, or a vinyl group, or $R^1$ and $R^3$, together with the atoms to which they are bonded, form a 5–12 membered ring; $R^{54}$, $R^{55}$, $R^{56}$, $R^{58}$, and $R^{65}$ are independently selected from the group consisting of H, alkyl groups, aryl groups, halogen, amino groups, alkoxy groups, hydroxy groups, and acid groups; $R^{62}$ represents an alkyl moiety; or $R^{65}$ and $R^{62}$ together represent the atoms necessary to complete a 5–12 membered ring. The method includes providing a cyclohexadiene derivative having the formula:

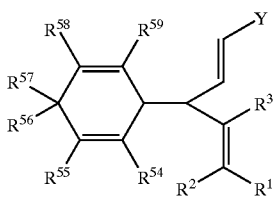

where $R^{57}$ is H, $R^{59}$ is independently selected from the group consisting of H, alkyl groups, aryl groups, halogens, amino groups, alkoxy groups, hydroxy groups, and acid groups, and Y is an electron withdrawing group. The cyclohexadiene derivative is then converted with hydrogenating and oxidizing agents under conditions effective to form a phenyl derivative having the formula:

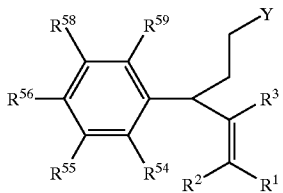

and the phenyl derivative is converted under conditions effective to produce the compound.

DETAILED DESCRIPTION OF THE INVENTION

As used herein, "alkyl" is meant to include linear alkyls, branched alkyls, and cycloalkyls, each of which can be substituted or unsubstituted. "Alkyl" is also meant to include lower linear alkyls (e.g., C1–C6 linear alkyls), such as methyl, ethyl, n-propyl, n-butyl, n-pentyl, and n-hexyl; lower branched alkyls (e.g., C3–C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3–C8 cycloalkyls), such as cyclopropyl, cyclobutyl, cyclopentyl, cyclohexyl, and the like. "Alkyl", as use herein, is meant to include unsubstituted alkyls, such as those set forth above, in which no atoms other than carbon and hydrogen are present. "Alkyl", as use herein, is also meant to include substituted alkyls. Suitable substituents include aryl groups (which may themselves be substituted), heterocyclic rings (saturated or unsaturated and optionally substituted), hydroxy groups, alkoxy groups (which is meant to include aryloxy groups (e.g., phenoxy groups)), thiol groups, alkylthio groups, arylthio groups, amine groups (unsubstituted, monosubstituted, or disubstituted, e.g., with aryl or alkyl groups), carboxylic acid groups, carboxylic acid derivatives (e.g., carboxylic acid esters, amides, etc.), phosphine groups, sulfonic acid groups, halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl".

As used herein, "alkylene" refers to a bivalent alkyl group, where alkyl has the meaning given above. Linear, branched, and cyclic alkylenes, as well as examples thereof, are defined in similar fashion with reference to their corresponding alkyl group. Examples of alkylenes include eth-1,1-diyl (i.e., —CH(CH$_3$)—), eth-1,2-diyl (i.e., —CH$_2$CH$_2$—), prop-1,1-diyl (i.e., —CH(CH$_2$CH$_3$)—), prop-1,2-diyl (i.e., —CH$_2$—CH(CH$_3$)—), prop-1,3-diyl (i.e., —CH$_2$CH$_2$CH$_2$—), prop-2,2-diyl (e.g. —C(CH$_3$)$_2$—), cycloprop-1,1-diyl, cycloprop-1,2-diyl, cyclopent-1,1-diyl, cyclopent-1,2-diyl, cyclopent-1,3-diyl, cyclohex-1,1-diyl, cyclohex-1,2-diyl, cyclohex-1,3-diyl, cyclohex-1,4-diyl, but-2-en-1,1-diyl, cyclohex-1,3-diyl, but-2-en-1,4-diyl, but-2-en-1,2-diyl, but-2-en-1,3-diyl, but-2-en-2,3-diyl. Also included in the meaning of the term "alkylene" are compounds having the formula —R'—R"—, where —R' represents a linear or branched alkyl group and R"— represents a cycloalkyl group, such as moieties having the formula:

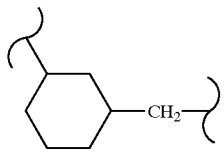

As used herein, "aryl" is meant to include aromatic rings, preferably having from 4 to 12 members, such as phenyl rings. These aromatic rings can optionally contain one or more heteroatoms (e.g., one or more of N, O, and S), and, thus, "aryl", as used herein, is meant to include heteroaryl moities, such as pyridyl rings and furanyl rings. The aromatic rings can be optionally substituted. "Aryl" is also meant to include aromatic rings to which are fused one or more other aryl rings or non-aryl rings. For example, naphthyl groups, benzimidazole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), hydroxy groups, alkoxy groups (which is meant to include aryloxy groups (e.g., phenoxy groups)), thiol groups, alkylthio groups, arylthio groups, amine groups (unsubstituted, monosubstituted, or disubstituted, e.g., with aryl or alkyl groups), carboxylic acid groups, carboxylic acid derivatives (e.g., carboxylic acid esters, amides, etc.), phosphine groups, sulfonic acid groups, halogen atoms (e.g., Cl, Br, and I), and the like.

As used herein, "arylene" is meant to include a bivalent aryl group in which both valencies are present on aromatic carbons. Examples of such groups include, for example, 1,3-phenylene, 1,4-phenylene, 5-methyl-1,3-phenylene, pyrid-2,3-diyl, pyrid-2,4-diyl, pyrid-2,5-diyl, pyrid-3,5-diyl, 1,3-naphthylene, 1,7-naphthylene, 1,8-naphthylene, 5,6,7,8-tetrahydro-1,3-naphthylene. "Arylene", as used herein, is also meant to include a bivalent group having the formula —R—R'—, where R is an alkyl group and R' is an aryl group. As the structure of —R—R'— indicates, one of the valencies is on the R (i.e., alkyl) portion of the —R—R'— moiety and the other of the valencies resides on the R' (i.e., aryl) portion of the —R—R'— moiety. Examples of this type of arylene moiety include moieties having the formulae:

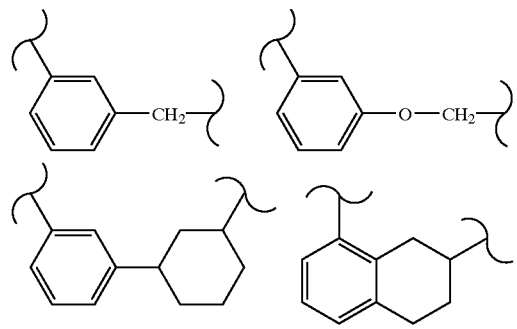

and the like.

As used herein, "alkoxy" is meant to include groups having the formula —O—R, where R is an alkyl or aryl group. They include methoxy, ethoxy, propoxy, phenoxy, 4-methylphenoxy, and the like.

As used herein, "electron withdrawing group" refers to those groups which are able to withdraw electron density from adjacent positions in a molecule, as determined, for example, by reference to the tables in the classical works which establish the classification of various substituents according to their electron withdrawing character. For example, reference may be made to the classification established by the Hammett scale, such as the one set forth in Gordon et al., *The Chemist's Companion,* New York: John Wiley & Sons, pp. 145–147 (1972), which is hereby incorporated by reference. Suitable electron-withdrawing groups include those having a para a value higher than or equal to about 0.2 or higher than or equal to about 0.3, with reference to the Hammett scale. Particular examples of electron withdrawing groups are moieties having the formulae —C(O)R, —SO$_2$R, and —P(O)RR', where R and R' are independently selected from an alkyl group, an aryl group, and an alkoxy group.

As used herein, "ring" refers to a homocyclic or heterocyclic ring which can be saturated or unsaturated. The ring can be unsubstituted, or it can be substituted with one or more substituents. The substituents can be saturated or unsaturated, aromatic or nonaromatic, and examples of suitable substituents include those recited above in the discussion relating to susbtituents on alkyl and aryl groups. Furthermore, two or more ring substituents can combine to form another ring, so that "ring", as used herein, is meant to include fused ring systems. In the case where the ring is saturated (i.e., in the case where each of the atoms making up the ring are joined by single bonds to other members of the ring), the ring may optionally include unsaturated (aromatic or nonaromatic) or saturated substituents.

The present invention relates to a compound which includes a first metal atom and second metal atom that are bonded to one another along an axis. This can be represented by the formula $M^1$—$M^2$, where $M^1$ and $M^2$ represent the first and second metal atoms, repectively, and the dash represents the bond and the bond axis. The compound also includes two carboxylate ligands. As used herein, "carboxylate ligands" means ligands which contain one or more carboxylate groups. As used herein, carboxylate groups mean groups having the formula:

which can be written with the following formula:

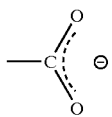

where the dashed line represents the delocalized electron. Alternatively, the carboxylate group can be expressed without showing the delocalized electron, as in the following formula:

In the present invention, each of the two carboxylate ligands includes two carboxylate groups, and these two carboxylate groups are bonded to each other via a moiety having the formula ("Formula I"):

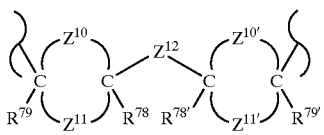

In Formula I, $Z^{10}$ and $Z^{11}$, together with the atoms to which they are bonded form a 3–12 membered ring, and $Z^{10'}$ and $Z^{11'}$, together with the atoms to which they are bonded form a 3–12 membered ring. Preferably, $Z^{10}$ and $Z^{10'}$ are the same, and each contains a heteroatom, such as a nitrogen, oxygen, or sulfur. More preferably, $Z^{10}$ and $Z^{10'}$ are the same, and each represents a single heteroatom selected from the group consisting a sulfur atom, an oxygen atom, and an optionally substituted nitrogen atom. Preferably, at least one of $Z^{10}$ and $Z^{10'}$ has the formula —NQ—, at least one of $Z^{11}$ and $Z^{11'}$ is an arylene or alkylene group, and Q is an electron withdrawing group. Still more preferably, both of $Z^{10}$ and $Z^{10'}$ has the formula —NQ—, both of $Z^{11}$ and $Z^{11'}$ is an alkylene group, and Q is an electron withdrawing group. Although one of $Z^{10}$ and $Z^{11}$ and/or one of $Z^{10'}$ and $Z^{11'}$ can represent a direct bond between the carbons to which they are attached, it is preferred that this not be the case and that none of $Z^{10}$, $Z^{11}$, $Z^{10'}$, and $Z^{11'}$ represents such a direct bond. $R^{78}$, $R^{78'}$, $R^{79}$, and $R^{79'}$ are independently selected from the group consisting of H, an alkyl group, and an aryl group. Preferably, each of $R^{78}$, $R^{78'}$, $R^{79}$, and $R^{79'}$ represents a hydrogen. $Z^{12}$ represents an alkylene or arylene group, preferably a substituted or unsubstituted 1,3-phenylene group.

As indicated in the formulae above, each of the two carboxylate groups includes a first carboxylate oxygen atom ("$O^1$"), a second carboxylate oxygen atom ("$O^2$"), and a carbon ("C") to which the $O^1$ and the $O^2$ are bonded thereby forming two $O^1$—C—$O^2$ moieties. In the compounds of the present invention, each $O^1$—C—$O^2$ moiety lies in and defines a plane which is substantially parallel to the $M^1$—$M^2$ bond axis. $O^1$ of each of the two carboxylate groups of each of the two carboxylate ligands is bonded to the first metal atom $M^1$; $O^2$ of each of the two carboxylate groups of each of the two carboxylate ligands is bonded to the second metal atom $M^2$. As used in this context, planes which are "substantially parallel" to the $M^1$—$M^2$ bond axis include those planes which do not intersect the $M^1$—$M^2$ bond axis or which intersect the $M^1$—$M^2$ bond axis at an angle of less than 20°, preferably less than 10°.

Each of the two carboxylate ligands further comprises at least two chiral centers. These centers, for example, can be included in one or more of $Z^{10}$, $Z^{11}$, $Z^{10'}$, and $Z^{11'}$, and/or they can be located at the carbon atoms to which $Z^{10}$, $Z^{11}$, $Z^{10'}$, and $Z^{11'}$ are bonded. The stereochemistry at these chiral moieties are selected such that the compound, taken as a whole, has $D_2$ symmetry. Molecules having $D_2$ symmetry are molecules which have a vertical $C_2$ axis and a set of two $C_2$ axes perpendicular to the vertical $C_2$ axis. $D_2$ symmetry is further described in, for example, Cotton et al., *Advanced Inorganic Chemistry*, 4th ed., New York: John Wiley & Sons, pages 28–46 (1980), which is hereby incorporated by reference.

Illustrative examples of such compounds and methods of making and using them are described below.

The present invention, in another embodiment thereof, relates to compounds having the formula ("Formula II"):

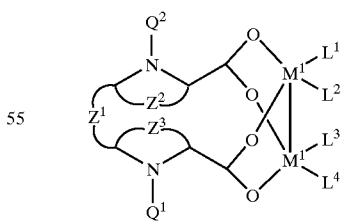

$M^1$ and $M^2$ are the same or different and are transition metal atoms or ions, examples of which include Sc, Y, the Lanthanides, the Actinides, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg metal atoms and ions. Preferably, $M^1$ and $M^2$ are the same or different and are selected from the group consisting of zero-valent Rh, zero-valent Ru, zero-valent Mo, zero-valent Pd, and zero-valent Re. More preferably, each of $M^1$ and $M^2$ are Rh.

$Z^2$ and $Z^3$, independently, are the atoms necessary to complete a 3–12 membered heterocyclic ring. Examples of such atoms include, for example: substituted or, preferably, unsubstituted alkylene moieties, such as those having the formula —$(CH_2)_i$—, where i is an integer from 1 to 8; and moieties having the formula —$(CH_2)_i$—X—$(CH_2)_j$—, where i and j each independently represent integers from 0 to 4 and X is a heteroatom, such as O, S, and $NR^{70}$, where $R^{70}$ is a substituted or unsubstituted alkyl, aryl, or heteroaryl group. Preferably, $Z^2$ and $Z^3$ are the same, and, more preferably, each of $Z^2$ and $Z^3$ have the formula —$CH_2CH_2$—.

$Z^1$ is an alkylene or arylene group. Illustratively, $Z^1$ can have the formula —$(CH_2)_i$—, where i is an integer from 1 to 8. Alternatively, $Z^1$ can have the formula —$(CH_2)_i$—X—$(CH_2)_j$—, where i and j each independently represent integers from 0 to 4 and X is a heteroatom, such as O, S, and $NR^{70}$, where $R^{70}$ is an alkyl or aryl group. Still alternatively, $Z^1$ can be a cycloalkyl moiety, such as cyclopent-1,3-diyl and cyclohex-1,3-diyl, which can be substituted or unsubstituted. Still alternatively, $Z^1$ can be an arylene moiety, such as a 1,3-phenylene or 1,3-naphthylene, or an heterocyclic moiety, such as a pyrid-3,5-diyl, pyrid-2,6-diyl, 2H-pyran-3,5-diyl, and tetrohydropyran-3,5-diyl moiety. Preferably, $Z^1$ is a 1,3-phenylene moiety.

$Q^1$ and $Q^2$ are the same or different and are electron withdrawing groups. Examples of $Q^1$, suitable for use in the practice of the present invention are moieties having the formulae —$C(O)R^1$, —$SO_2R^1$, and —$P(O)R^1R^{1'}$, and examples of suitable $Q^2$ include moieties having the formulae —$C(O)R^2$, —$SO_2R^2$, and —$P(O)R^2R^{2'}$. In these formulae, each of $R^1$, $R^{1'}$, $R^2$, and $R^{2'}$ is independently selected from an alkyl group, an aryl group, and an alkoxy group. Preferably, $Q^1$ has the formula —$SO_2R^1$; $Q^2$ has the formula —$SO_2R^2$; and $R^1$ and $R^2$ are the same or different and are substituted or unsubstituted alkyl or aryl groups. More preferably, $Q^1$ has the formula —$SO_2R^1$; $Q^2$ has the formula —$SO_2R^2$; and each of $R^1$ and $R^2$ is independently selected from the group consisting of 4-(t-butyl)phenyl, 2,4,6-trimethylphenyl, and 2,4,6-triisopropylphenyl.

In the above Formula II, $L^1$ and $L^3$, taken together, represent a —O—$CR^{13}$—O— moiety, and $L^2$ and $L^4$, taken together, represent a —O—$CR^{14}$—O— moiety. In these moieties, $R^{13}$ and $R^{14}$ can be the same or they can be different, and each is independently selected from the group consisting of alkyl groups and aryl groups. Alternatively, $R^{13}$ and $R^{14}$ can represent alkylene or arylene groups that are directly or indirectly bonded to one another. In the latter case, the compound of the present invention can be expressed as the following formula ("Formula III"):

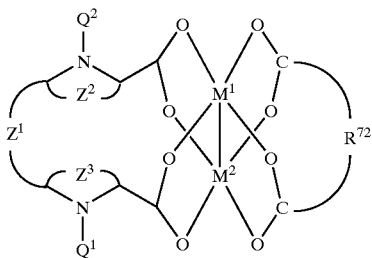

where $R^{72}$ represents an alkylene or arylene group. Preferably, $R^{13}$ and $R^{14}$, taken together, represent an alkylene or arylene group such that the compound of the present invention has the following formula ("Formula IV")

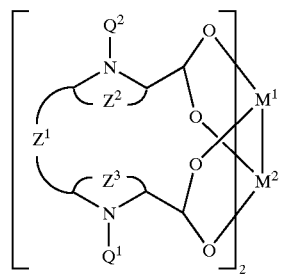

The above-described compounds have at least four chiral centers (i.e., at least the two carbons to which $Z^2$ is bonded and at least the two carbons to which $Z^3$ is bonded are chiral). The present invention is not meant to be limited to any particular set of configurations at the compound's chiral centers, and the structures given above are meant to be broadly read to include any and all possible collections of chiralities. For example, compounds having Formula I are meant to include (i) compounds having the formula ("Formula V"):

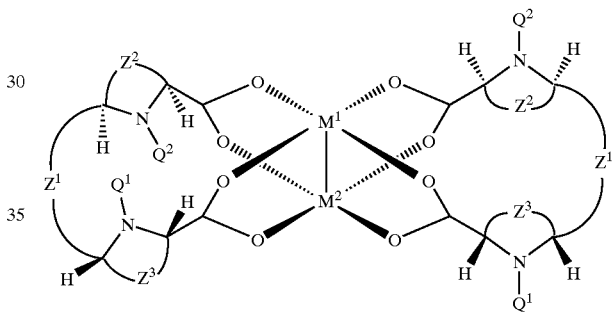

and (ii) compounds having the formula ("Formula VI"):

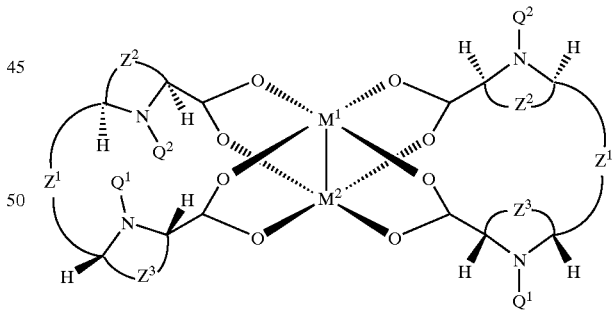

Each of the compounds having Formulae V and VI can be present alone (i.e., as a pure diastereoisomer) or they can be present in a mixture with one or more different diastereoisomers. Preferably, the compound is substantially free of other diastereoisomers. In this context, "substantially free of other disatereoisomers" means that the molar ratio of other diastereoisomers to the compound is less than 40%, preferably less than 30%, more preferably less that 20%, still more preferably less that 10%, still more preferably less that 5%, still more preferably less that 2%, and still more preferably less that 1%.

Preferred examples of compounds having Formula V and VI, respectively, are those having the formula ("Formula VII"):

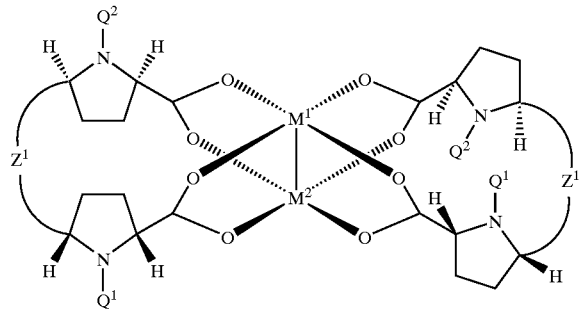

and those having the formula ("Formula VIII"):

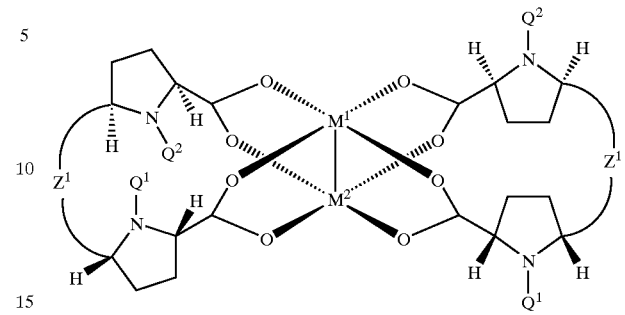

More preferred examples of compounds having Formula V and VI, respectively, are those having the formula ("Formula IX"):

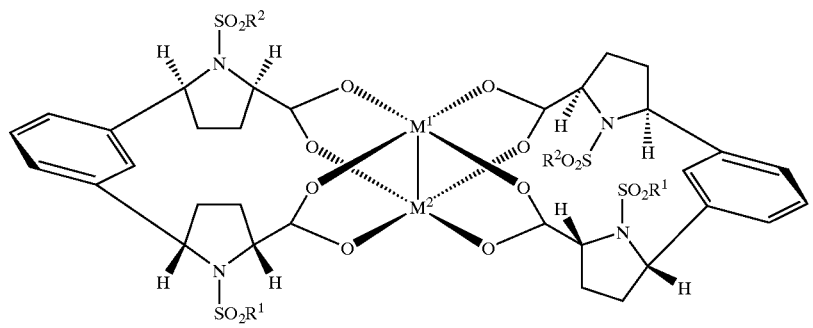

and those having the formula ("Formula X"):

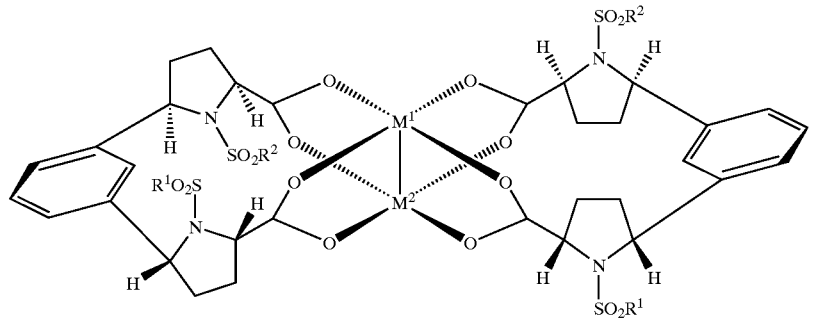

In Formula IX and Formula X, $R^1$ and $R^2$ are the same or different and are alkyl or aryl groups.

Compounds of the present invention can be made by a variety of methods. One particularly suitable method, which is the subject of another aspect of the. present invention, is illustrated below.

Compounds having Formula II can be prepared from ligands having the formula ("Formula XI"):

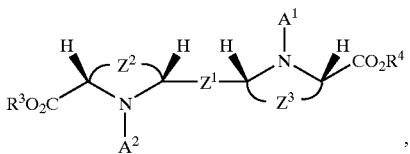

from ligands having the formula ("Formula XII")

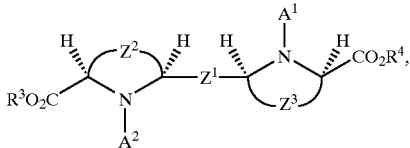

or from combinations of these ligands. In each of these formulae, $R^3$ and $R^4$ is independently selected from the group consisting of hydrogen, an alkyl group, or an aryl group, and each of $A^1$ and $A^2$ is independently selected from the group consisting of a hydrogen atom and an electron withdrawing group. Preferred ligands are those in which $R^3$ and $R^4$ are both hydrogen atoms. However, ligands containing other groups in the $R^3$ and $R^4$ positions can be employed, for example, by replacing these groups with hydrogen atoms using, for example, conventional ester hydrolysis methods, such as room temperature saponification with a strong base (e.g., lithium hydroxide). Preferred ligands are those in which $A^1$ and $A^2$ are both electron withdrawing groups, such as —C(O)R$^2$, —SO$_2$R$^2$, or —P(O)R$^2$R$^{2'}$ groups where each of $R^1$, $R^{1'}$, $R^2$, and $R^{2'}$ is, independently, an alkyl group, an aryl group, or an alkoxy group. However, ligands in which one or both $A^1$ and $A^2$ are hydrogen atoms can be used, for example, by replacing the hydrogen atoms with electron withdrawing groups using, for example, conventional acylation, sulfonation, or phosphonylation procedures.

The ligands are converted to the compound of Formula II using a bis-metal salt under conditions effective to produce the compound of Formula II. Suitable bis-metal salts are those having the formula $M^1M^2(OOCR^5)_4$ in which $R^5$ is an alkyl group or an aryl group and in which $M^1$ and $M^2$ are as defined above. Preferably, $M^1$ and $M^2$ are the same, and each of the $R^1$ groups is a C1–C6 alkyl. More preferably, each of $M^1$ and $M^2$ is Rh, and each of the OOCR$^5$ groups represents an acetate group, in which case the bis-metal salt has the formula $Rh_2(OOCCH_3)_4$.

The aforementioned conversion can be advantageously carried out by contacting the bis-metal salt with the ligand for a period of time and at a temperature effective to produce the compound of Formula II. This can be done, for example by pre-forming the bis-metal salt and then contacting the preformed bis-metal salt with the ligand. Alternatively, the bis-metal salt can be produced in situ, for example, from an appropriate metal salt. This latter method is particularly advantageous in the case where $M^1$ and $M^2$ are the same. For example, in the case where both $M^1$ and $M^2$ are Rh, the method can be carried out by mixing the ligand with rhodium diacetate rather than with the preformed dirhodium tetraacetate. Irrespective of whether the bis-metal salt is preformed or permitted to form in situ, the reaction is typically carried out in an suitable solvent (e.g., an aromatic solvent, such as benzene, toluene, xylenes, or, preferably, a chlorinated benzene, such as chlorobenzene or dichlorobenzene, or a hydrocarbon solvent, such as hexanes, heptane, iso-octane, or n-octane), with stirring, under reflux, and/or with some other type or agitation, for from about 2 hours to about 10 days, preferably from about 1 day to about 5 days, and at a temperature of from about 30° C. to about 150° C., preferably from about 120° C. to about 140° C. Preferably, the reaction solvent is chosen so as to permit the reaction to be carried out at a reflux temperature of from about 120° C. to about 140° C. Furthermore, preferably, the reaction is carried out in the presence of a compound capable of neutralizing acids. Where the reaction is carried out under reflux, this can be advantageously achieved by refluxing the solvent through a soxhlet extraction apparatus containing calcium carbonate or another acid-neutralizing compound. The resulting product can be separated from the reaction mixture by conventional means (e.g., by precipitation and filtering and/or by removing the solvent, preferably under vacuum), and it can be optionally purified, for example, by crystallization or chromatorgraphy.

The ligands used in the above procedure can be produced using a number of methods. Illustratively, N-substituted ligands having the formula ("Formula XIII"):

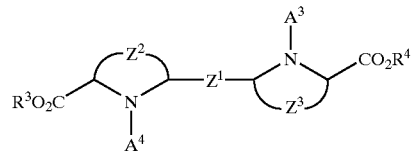

in which $A^3$ and $A^4$ are independently selected from the group consisting of —C(O)R$^2$, —SO$_2$R$^2$, and —P(O)R$^2$R$^{2'}$ and in which $Z^1$, $Z^2$, $Z^3$, $R^1$, $R^{1'}$, $R^2$, $R^{2'}$, $R^3$, and $R^4$ are defined as they were above in the discussion relating to Formulae XI and XII, can be produced by the following method. The method includes providing an N-unsubstituted compound having the formula ("Formula XIV"):

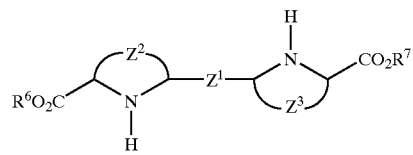

wherein each of $R^6$ and $R^7$ is independently selected from an alkyl group or an aryl group, and converting the N-unsubstituted compound to the N-substituted compound with an acylating agent, a sulfonylating agent, or a phosphonylating agent. Examples of suitable sulfonating agents include arylsulfonyl chlorides, such as benzenesulfonyl chloride, 4-methylbenzenesulfonyl chloride, and 2,4,6-triisopropylbenzenesulfonyl chloride. Typically this conversion is carried out by contacting at least two equivalents, preferably from about 2.3 to about 4 equivalents, of acylating agent, sulfonylating agent, or phosphonylating agent with the N-unsubstituted compound at a temperature of from about 10° C. to 100° C., preferably at about room temperature, for from about 15 minutes to about 10 days, preferably for from about 3 hours to about 5 days. The reaction can be carried out neat (i.e., without the use of solvent), or it can be carried out in a suitable inert solvent, such an aromatic solvent (e.g., benzene and toluene), an alkane solvent (e.g., hexanes), a chlorinated solvent (e.g., chlorobenzene or chloroform), or a ketone solvent (e.g., acetone). In some cases, the reaction can be quite vigorous and may benefit from slow addition (e.g., dropwise addition) of the acylating agent, sulfonylating agent, or phosphonylating agent to the N-unsubstituted compound while cooling the reaction mixture, with for example, an ice-water bath.

Typically, these reactions produce strong acid, which is advantageously neutalized. Neutralization can be carried out by carrying out the reaction in the presence of, for example, an alkali metal carbonate or bicarbonate and/or by washing the reaction mixture with, for example, alkali metal carbonate or bicarbonate. The N-substituted compound can be separated from the reaction mixture by, for example, extraction, precipitation, and/or filtration, and the N-substituted compound, thus separated, can be purified by standard methods, such as recrystallization or chromatography. The method discussed above for the preparation of compounds having Formula XIII can be readily adapted to prepare substantially diasteriomerically pure compounds having Formula XI and Formula XII by using, respectively, N-unsubstituted compounds having the formula ("Formula XV"):

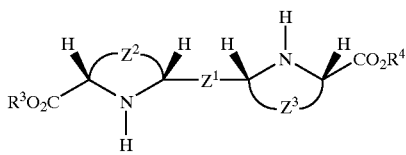

and having the formula ("Formula XVI"):

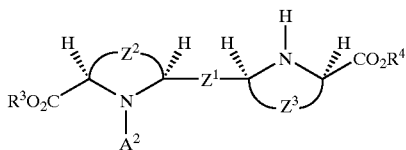

N-unsubstituted compounds having Formula XIV can be advantageously prepared by the following method, to which the present invention also relates. The method includes providing an unsaturated heterocyclic compound having the formula ("Formula XVII"):

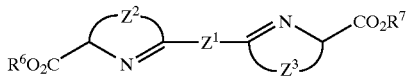

and converting the unsaturated heterocyclic compound to the N-unsubstituted compound using hydrogenation. Typically, the hydrogenation reaction is carried out by contacting the unsaturated heterocyclic compound with a hydrogenating agent, such as hydrogen gas, in the presence of a hydrogenation catalyst, for a suitable length of time (e.g., from about 30 minutes to about 48 hours), at a suitable temperature (e.g. from about 10° C. to about 100° C., preferably at about room temperature), at a suitable pressure (e.g., from-about atmospheric pressure to about 100 psi), and in a suitable solvent (e.g., ether solvents, such as tetrahydrofuran or diethyl ether; alkane solvents, such as hexanes; aromatic solvents, such as benzene or toluene; and alcohol solvents, such as ethanol or isopropanol). It has been found that platinum oxide (e.g., $PtO_2$) is a particularly effective catalyst for this reaction, although other hydrogenation catalysts, such as those described in Larock in *Comprehensive Organic Transformations*, New York: Wiley-VCH (1999) ("Larock"), particularly at pp. 7–12, which is hereby incorporated by reference, can be used. Following the reaction, the N-unsubstituted compound is typically separated from catalyst by filtration, and the solvent is then removed, for example, under reduced pressure. Further purification of the resulting N-unsubstituted compound can be carried out by, for example, recrystallization or chromatography. Using the methods set forth above, N-unsubstituted compounds having Formula XV and Formula XVI can be prepared, respectively, from unsaturated heterocyclic compounds having the formula ("Formula XVIII"):

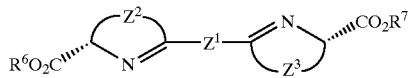

and having the formula ("Formula XIX"):

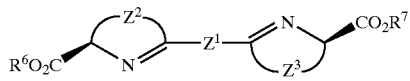

where $Z^1$, $Z^2$, $Z^3$, $R^3$, $R^4$, $R^6$, and $R^7$ have the meanings set forth above. Preferred unsaturated heterocyclic compounds are those in which $Z^1$ is a 1,3-phenylene group.

In some situations, it is particularly desirable to convert the ester groups (represented by $COOR^6$ and $COOR^7$) to the corresponding acid groups (represented by $COOR^3$ and $COOR^4$) prior to converting the N-unsubstituted compound to the N-substituted compound. As indicated above, this can be done by conventional deesterification methods, such as for example, saponification. Such saponification can advantageously be carried out on the crude N-unsubstituted compound resulting from the above-described hydrogenation procedure. One suitable saponification method is to reflux the N-unsubstituted compound with an excess of strong alkali metal base in water or a water/solvent mixture. For example, the N-unsubstituted compound can be dissolved and/or suspended in a mixture of tetrahydrofuran, ethanol, and water containing from about a 5 to about a 100 molar excess of lithium hydroxide, and the resulting mixture can be stirred at room temperature or heated, preferably at reflux, for from about 2 hours to about 72 hours. The progress of this reaction can be monitored, for example, by thin layer chromatography to determine when saponification has reached the desired level of completion.

Unsaturated heterocyclic compounds having Formula XVII can be advantageously prepared using the following method, to which the present invention also pertains. In this method, a cyclic ketone having the formula ("Formula XX"):

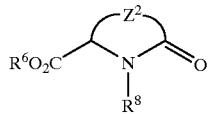

where $R^8$ is an amine-protecting group, is converted to the N-unsaturated heterocyclic compound with a bis-lithium compound having the formula $Z^1Li_2$. For example, in the case where $Z^1$ is a 1,3-phenylene moiety, the bis-lithium compound used in this reaction is 1,3-dilithiobenzene.

"Amine protecting group", as used herein refers to any group known in the art of organic synthesis for the protection of amine groups. Suitable amine protecting groups are listed in Greene et al., *Protective Groups in Organic Synthesis*, New York: John Wiley & Sons (1991), which is hereby incorporated by reference. Examples of amine protecting groups include, but are not limited to, acyl type amine protecting groups, such as formyl, trifluoroacetyl, phthalyl, and p-toluenesulfonyl; aromatic carbamate type amine protecting groups, such as benzyloxycarbonyl and substituted benzyloxycarbonyls, 1-(p-biphenyl)-1-methylethoxy-carbonyl, and 9-fluorenylmethyloxycarbonyl; aliphatic carbamate type amine protecting groups, such as tert-butyloxycarbonyl ("BOC"), ethoxycarbonyl, diisopropylmethoxycarbonyl, and allyloxycarbonyl; cyclic alkyl carbamate type amine protecting groups, such as cyclopentyloxycarbonyl and adamantyloxycarbonyl; alkyl type amine protecting groups, such as triphenylmethyl (i.e., trityl) and benzyl; trialkylsilane type amine protecting groups, such as trimethylsilane; and thiol containing type amine protecting groups, such as phenylthiocarbonyl and dithiasuccinoyl. BOC is the preferred amine protecting group.

The reaction of the cyclic ketone with the bis-lithium compound is preferably carried out using conventional lithium alkylation procedures. Typically the reaction is carried out in an inert solvent (e.g., tetrahydrofuran or diethyl ether) and in the strict absence of water by slowly adding (e.g., over the course of from about 30 minutes to about 2 hours) an excess (e.g., from about 2 to about 10 equivalents) of the cyclic ketone (preferably dissolved in inert solvent) to the dilithium compound (preferably also dissolved in the inert solvent) at reduced temperatures (e.g., from about 0° C. to about −78° C.). The resulting mixture is then typically permitted to warm to room temperature, with stirring, and stirring is continued for from about 2 hours to about 4 days, preferably from about 15 hours to about 30 hours. After the reaction is complete, the mixture is typically poured into water and extracted with an organic solvent (e.g., ethyl acetate). The organic solvent is dried (e.g., over $MgSO_4$) and removed, advantageously under reduced pressure.

The amine protecting group can then be cleaved using conventional methods, such as, in the case where the amine protecting group is BOC, by treating the reaction product with an excess (e.g., from about 20 to about 100 equivalents, based on the amount of dilithium compound employed) of trifluoroacetic acid ("TFA"). This treatment is typically carried out in a suitable solvent (e.g., a chlorinated hydrocarbon, such as dicloromethane or chloroform) for from about 30 minutes to about 48 hours at from about 10° C. to about 100° C., preferably at about room temperature. Subsequently, the excess acid is neutralized (e.g., with bicarbonate), the solvent is removed (e.g., under reduced pressure), and the unsaturated heterocyclic compound is optionally further purified (e.g., by recrystallization and/or chromatography).

Many suitable dilithium compounds can be purchased commercially. Alternatively, these compounds can be prepared by conventional methods, such as those set forth in Fossatelli et al., "1,3-Dilithiobenzene and 1,4-Dilithiobenzene," *Rec. Trav. Chim. Pays-Bas*, 113:527–528 (1994), which is hereby incorporated by reference.

Cyclic ketones that can be used to prepare the unsaturated heterocyclic compound, as described above, can be obtained from commercial sources, or, alternatively, they can be produced, for example, using the methods described in, for example, Ezquerra et al., "Stereoselective Reactions of Lithium Enolates Derived From N-BOC Protected Pyroglutamic Esters," *Tetrahedron*, 49:8665–8678 (1993), which is hereby incorporated by reference.

In the case where the N-unsaturated heterocyclic compound has Formula XVIII, it is advantageous to employ a cyclic ketone having the formula ("Formula XXI"):

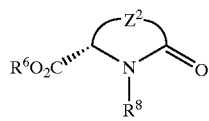

In the case where the N-unsaturated heterocyclic compound has Formula XIX, it is advantageous to employ a cyclic ketone having the formula ("Formula XXII"):

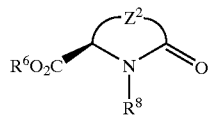

The above compounds (e.g., those represented by Formulae II, III, IV, V, VI, VII, VIII, IX, and X as well as those containing the moiety denoted Formula I) can be used to effect a variety of organic transformations. One such illustrative organic transformation is the C—H insertion reaction, such as those C—H insertion reactions in which bis-transition metal catalysts have been previously employed, especially in cases where substantially diasteriomerically pure products are desired. Several of such C—H insertion reactions are described below. However, nothing herein should be construed as meaning that the reactions described below must be carried out with the compounds described above.

The present invention further relates to a method of producing a compound having the formula ("Formula XXIII"):

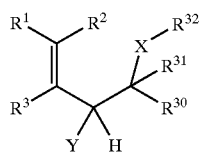

$R^1$, $R^2$, and $R^3$ are independently selected from H, alkyl, aryl, or vinyl, or $R^1$ and $R^3$, together with the atoms to which they are bonded, form a 5–12 membered ring, such as a cyclohexene ring, or a cyclohexa-1,3-diene ring. The method is particularly well-suited for preparing compounds in which $R^1$ and $R^3$, together with the atoms to which they are bonded, form an aromatic ring, such as a phenyl ring, in which case the compound produced by this method has the formula ("Formula XXIV"):

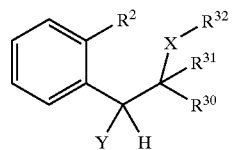

Y is an electron withdrawing group, examples of which include moieties having the formulae: $-C(O)R^{77}$, $-SO_2R^{77}$, and $-P(O)R^{77}R^{77'}$. In these formulae, each of $R^{77}$ and $R^{77'}$ is independently selected from an alkyl group, an aryl group, and an alkoxy group. Preferably, Y has the formula $CO_2R^{12}$ where $R^{12}$ is an alkyl group or an aryl group.

X is $CH_2$, O, or $NR^{11}$, and $R^{11}$ is H, an alkyl group, an aryl group, an acyl group, an alkoxycarbonyl group, or a silyl group having the formula $-SiR^{33}R^{34}R^{35}$, where $R^{33}$, $R^{34}$, and $R^{35}$ are independently selected from an alkyl group and an aryl group.

Each of $R^{30}$ and $R^{31}$ is independently selected from the group consisting of H, alkyl, aryl, and vinyl. $R^{32}$ is an alkyl group, an aryl group, an acyl group, an alkoxycarbonyl group, or a silyl group having the formula —SiR$^{36}$R$^{37}$R$^{38}$, where $R^{36}$, $R^{37}$, and $R^{38}$ are independently selected from an alkyl group and an aryl group. Alternatively, $R^{31}$ and $R^{32}$, together with the atoms to which they are bonded, can form a 5–12 membered ring, such as a cyclopentyl or cyclohexyl ring (in the case where X is —CH$_2$—), a piperidinyl ring (in the case where X is N), or a tetrahydrofuranyl or a tetrahydropyranyl ring (in the case where X is O). Illustratively, the method of the present invention is well-suited for forming compounds having Formula XXIV in which X is not CH$_2$ when each of $R^{30}$ and $R^{31}$ is H.

The method includes providing a diazo compound having the formula ("Formula XXV"):

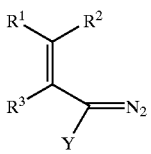

in which $R^1$, $R^2$, $R^3$, and Y have the same meanings as given above with reference to Formula XXIV. The method further includes converting the diazo compound with a compound having the formula ("Formula XXVI"):

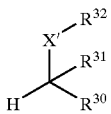

in the presence of a bis-transition metal catalyst and under conditions effective to produce the compound. In compound XXVI, $R^{30}$, $R^{31}$, and $R^{32}$ are defined as they are above with regard to Formula XXIV. When, in the desired product, X is CH$_2$ or O, X' in Formula XXVI is CH$_2$ or O, respectively. When, in the desired product, X is NR$^{11'}$, X' in Formula XXII is NR$^{11'}$ and R$^{11'}$ is an alkyl group, an aryl group, an acyl group, an alkoxycarbonyl group, or a silyl group (e.g., a triarylsilyl group, or a trialkylsilyl group). It is particularly preferred that, when X' represents an NR$^{11'}$ group, R$^{11'}$ represents an alkoxycarbonyl amine protecting group, such as BOC.

Suitable bis-transition metal catalysts for use in this reaction include, for example, catalysts having the formula L$_4$M—ML$_4$ where each of the L's is the same or different and represents a suitable ligand (e.g., an oxygen from an acetate moiety) and each of the M's is the same or different and represents a transition metal (e.g., Rh or Ru). Dirhodium and diruthenium catalysts, especially dirhodium or diruthenium tetracarboxylate catalysts, are preferred.

Illustrative dirhodium or diruthenium tetracarboxylate catalysts are those having the formula ("Formula XXVII"):

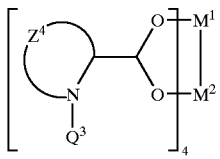

In Formula XXVII, each of $M^1$ and $M^2$ is Rh or Ru. $Z^4$ represents the atoms necessary to complete a 3–12 membered heterocyclic ring, such as an alkylene moiety (e.g., a —CH$_2$CH$_2$CH$_2$— moiety). $Q^3$ is an electron withdrawing group, such as a group having the formulae —C(O)R$^9$, —SO$_2$R$^9$, or —P(O)R$^9$R$^9$, where each of R$^9$ and R$^{9'}$ is independently selected from an alkyl group, an aryl group, and an alkoxy group. In cases where the desired product of Formula XXIII is substantially diasteriomerically pure, it is advantageous to use a substantially chirally pure catalyst, such as a dirhodium or diruthenium tetracarboxylate catalyst having the formula ("Formula XXVIII"):

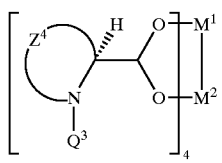

More preferably, the dirhodium or diruthenium tetracarboxylate catalyst having Formula XXVIII has D$_2$ symmetry.

Specific examples of suitable compounds having Formulae XXVII and XXVIII include: Rh$_2$(DOSP)$_4$, which is a compound having Formula XXVII in which each of $M^1$ and $M^2$ is Rh, $Z^4$ is a —CH$_2$CH$_2$CH$_2$— group, and Q$^3$ represents a 4-dodecylphenylsulfonyl moiety; Rh$_2$(S-DOSP)$_4$, which is a compound having Formula XXVIII in which each of $M^1$ and $M^2$ is Rh, $Z^4$ is a —CH$_2$CH$_2$CH$_2$— group, and Q$^3$ represents a 4-dodecylphenylsulfonyl moiety; Rh$_2$(TBSP)$_4$, which is a compound having Formula XXVII in which each of $M^1$ and $M^2$ is Rh, $Z^4$ is a —CH$_2$CH$_2$CH$_2$— group, and Q$^3$ represents a 4-t-butylphenylsulfonyl moiety; and Rh$_2$(S-TBSP)$_4$, which is a compound having Formula XXVIII in which each of $M^1$ and $M^2$ is Rh, $Z^4$ is a —CH$_2$CH$_2$CH$_2$— group, and Q$^3$ represents a 4-t-butylphenylsulfonyl moiety. These and other illustrative compounds having Formulae XXVII and XXVIII are described in greater detail in Davies, "Rhodium-Stabilized Vinylcarbenoid Intermediates in Organic Synthesis," *Current Organic Chemistry*, 2:463–488 (1998) ("Davies"), which is hereby incorporated by reference.

Particularly suitable bis-transition metal catalysts for carrying out the conversion of XXV with XXVI are those having Formulae II, III, IV, V, VI, VII, VIII, IX, and X, as defined and discussed above, particularly where $M^1$ and $M^2$ are Rh or Ru. Other particularly suitable bis-transition metal catalysts for carrying out the conversion of XXV with XXVI are chiral dirhodium or diruthenium catalysts, especially those which include a first metal atom and a second metal atom that are bonded to one another along an axis and two carboxylate ligands. Each of the two carboxylate ligands includes two carboxylate groups bonded to each other via a moiety having Formula I. Each of the two carboxylate groups includes a first carboxylate oxygen atom ("O$^1$"), a second carboxylate oxygen atom ("O$^2$"), and a carbon ("C") to which the O$^1$ and the O$^2$ are bonded thereby forming two O$^1$—C—O$^2$ moieties, and each O$^1$—C—O$^2$ moiety defines a plane which is substantially parallel to the axis. O$^1$ of each of the two carboxylate groups of each of the two carboxylate ligands is bonded to the first metal atom; O$^2$ of each of the two carboxylate groups of each of the two carboxylate ligands is bonded to the second metal atom; each of the two carboxylate ligands further comprises at least two chiral centers; and the compound has D$_2$ symmetry. Such bis-transition metal catalysts are discussed in greater detail above.

Typically, the reaction is carried out by mixing the catalyst with the compound of Formula XXVI. In the case where the compound of Formula XXVI is a liquid (e.g., in the case where the compound of Formula XXVI is tetrahydrofuran, tetrahydropyran, pyrrolidine, piperidine, cyclopentane, cyclohexane, etc.), this can be effected without the use of additional solvent. Alternatively, the mixture can be formed using an inert solvent or a solvent which is significantly less reactive toward the diazo compound of Formula XXV than is the compound of Formula XXVI. As an example, it has been found that when the compound of Formula XXVI is tetrahydrofuran, the catalyst and tetrahydrofuran can be mixed neat (i.e., without the use of additional solvent), or cyclohexane can be used as a reaction medium. The amount of catalyst employed is not critical to the practice of the present invention. Typically, the mole ratio of the catalyst to the compound of Formula XXVI is from about 1:10,000 to about 1:20, preferably from about 1:500 to about 1:50, and more preferably from about 1:200 to about 1:100.

Once the catalyst and compound of Formula XXVI are mixed, the diazo compound of Formula XXV is added, preferably with stirring. Addition can be carried out in a single portion, continuously, or batchwise. Slow, dropwise addition, using, for example, a syringe pump, is frequently advantageous. The amount of diazo compound of Formula XXV added is generally dependent on the amount of the compound of Formula XXVI present in the reaction mixture. Typically the mole ratio of the compound of Formula XXVI to the diazo compound of Formula XXV is from about 1:10 to about 10:1, preferably from about 6:1 to about 1:1, more preferably from about 4:1 to about 2:1. The addition can be carried out at any suitable temperature from the freezing point to the boiling point of the solvent and/or the compound of Formula XXVI. Typically, the addition is carried out from about −50° C. to about 60° C. Room temperature addition and addition at about 10° C. have been found to be advantageous. Optimization of reaction conditions, including temperature of addition, is more important when diastereomerically pure product is desired. Generally, formation of diastereomerically pure product is favored by lower addition temperatures (e.g., from about −50° C. to about 10° C.).

Applicants have unexpectedly discovered that, when the reaction of the present invention is carried out substantially in the absence of oxygen, the resulting product has significantly improved yield when compared to reactions which are not carried out substantially in the absence of oxygen. As used herein, "substantially in the absence of oxygen" means that the liquid reactants and solvents (if any) employed in carrying out the reaction are degassed, for example by bubbling an inert gas (e.g., nitrogen or argon) therethrough, that the reaction is carried out under blanket of inert gas or under vacuum, and that all transfers are carried out such that ambient air is excluded (e.g., by using rubber septums, gas tight syringes, and the like). Illustratively, applicants have unexpectedly discovered that when X is O or $CH_2$, when $R^1$ and $R^3$, together with the atoms to which they are bonded, form a 5–12 membered ring, and when $R^{31}$ and $R^{32}$, together with the atoms to which they are bonded, form a 5–12 membered ring, carrying out the reaction substantially in the absence of oxygen produces a product having significantly improved diastereoisomeric purity. When carrying out these reactions substantially in the absence of oxygen, it is advantageous to use a chiral catalyst, preferably a chiral catalyst having $D_2$ symmetry.

The conversion of the compound of Formula XXV with a compound of Formula XXVI to produce a compound of Formula XXIII described above is particularly suitable for preparing compounds having the formula ("Formula XXIX"):

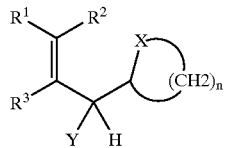

In this case, the conversion of the diazo compound of Formula XXV is carried out with a cyclic compound having the formula ("Formula XXX"):

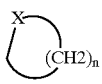

in which X' is defined as above and n is 3–10. In this embodiment, $R^1$ and $R^3$, together with the atoms to which they are bonded, preferably form a phenyl ring, and Y preferably has the formula —$CO_2R^{10}$ where $R^{10}$ is an alkyl or aryl group. The method is particularly suitable for making compounds in which X is $NR^{11}$ and in which n is 3 or 4. The method is also particularly suitable for making compounds having the formula ("Formula XXXI"):

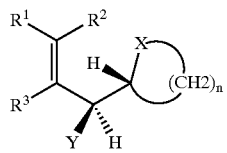

in which case the bis-transition metal catalyst employed is a chiral bis-transition metal catalyst. For example, by using the S-isomer of compounds having Formulae II, III, IV, V, VI, VII, VIII, IX, or X, as defined and discussed above (particularly where $M^1$ and $M^2$ are Rh or Ru), compounds of Formula XXXI which are substantially diasteriomerically pure (e.g., >80% ee, >90% ee, >95% ee, >98% ee, and/or >99% ee) can be prepared. Particularly preferred compounds having Formula XXXI are those in which X is $NR^{11}$, n is 3, Y is $CO_2R^{12}$, $R^{12}$ is alkyl or aryl, and $R^1$ and $R^3$, together with the atoms to which they are bonded, form an aromatic ring. Still more preferred are those compounds of Formula XXXI in which X is NH, $R^{12}$ is a methyl group, and $R^1$ and $R^3$, together with the atoms to which they are bonded, form a phenyl ring. Such compounds have the formula ("Formula XXXII"):

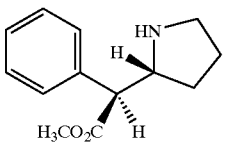

which is also referred to as threo methylphenidate and which is believed to be the biologically active form of RITALIN™.

The method of the present invention can also be used to prepared compounds having Formula XXIII in which X is $NR^{11}$ and in which $R^{31}$ and $R^{32}$, together with the atoms to which they are bonded represent a ring having the formula ("Formula XXXIII"):

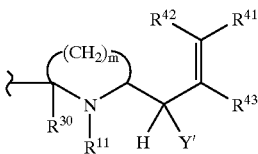

where $R^{30}$ is H. That is, the method can be used to prepare compounds having the formula ("Formula XXXIV"):

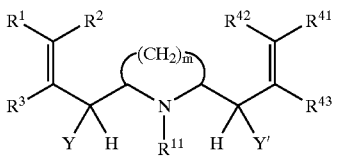

In these formulae, $R^{41}$, $R^{42}$, and $R^{43}$ are independently selected from H, alkyl, aryl, or vinyl, or $R^{41}$ and $R^{43}$, together with the atoms to which they are bonded, form a 5–12 membered ring. Y' is an electron withdrawing group, for example, the electron withdrawing groups discussed above with regard to Y, and m is 2–9. The reaction involves providing a diazo compound having Formula XXV and converting the diazo compound with a cyclic amine having the formula ("Formula XXXV"):

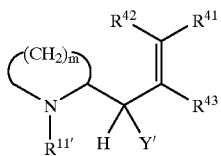

in the presence of a bis-transition metal catalyst and under conditions effective to produce the compound. Suitable conditions for this reaction are the same as the ones discussed above with regard to the conversion of compounds of Formula XXV with compounds of Formula XXVI. By using a chiral catalyst, compounds having the formula ("Formula XXXVI"):

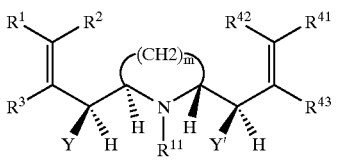

can be produced.

A variety of methods can be used to prepare the cyclic amine having Formula XXXV, but the preferred method is the one described above with regard to preparing compounds having Formula XXIX using diazo compounds of Formula XXV, cyclic compounds of Formula XXX, and a bis-transition metal catalyst. Rather than running the reaction in two steps (i.e., by first reacting a diazo compounds of Formula XXV with a cyclic compound of Formula XXX in which X is N to produce a cyclic amine having Formula XXIX and then reacting the cyclic amine having Formula XXIX with a diazo compound having Formula XXV to produce the desired compound of Formula XXXIV), the reaction can be carried out in a single step by, for example, contacting the cyclic compound of Formula XXX in which X is N with at least two equivalents of a diazo compound of Formula XXV. The reaction conditions suitable for carrying out this one step reaction are the same as those discussed above with regard to the two step method. Preferably, during the first part of the reaction (i.e., during the addition of the first half of the diazo compound having Formula XXV), the reaction is carried out with cooling (e.g., from about –50° C. to about 0° C.). Then the reaction mixture is warmed, and the second part of the reaction (i.e., during the addition of the second half of the diazo compound having Formula XXV) is carried out at elevated temperatures (e.g., from about 20° C. to about 100°0 C.). Alkanes having melting points of less than about –50° C. and boiling points greater than about 60° C. are the preferred solvents for this reaction.

The compounds prepared by the above method (i.e., compounds having Formulae XXIII, XXIV, XXIX, XXXI, XXXII, XXXIV, and XXXVI) are appropriately functionalized for further conversion by, for example, ester reduction or Grignard addition to highly functionalized bases. In the case where a chiral catalyst is employed, e.g., the S-isomer of compounds having Formulae II, III, IV, V, VI, VII, VIII, IX, or X, as defined and discussed above (particularly where $M^1$ and $M^2$ are Rh or Ru), these compounds can be used as $C_2$ symmetric bases, or, as indicated above, they can be further converted (e.g., by ester reduction or Grignard addition) to highly functionalized $C_2$ bases. $C_2$ bases are very useful for controlling stereochemistry in organic synthesis, for example, as described in Takahata et al., "New Entry to C2 Symmetric Trans-2,6-bis(hydroxymethyl) piperidine Derivatives Via the Sharpless Asymmetric Dihydroxylation," *Tetrahedron-Asymmetry*, 6:1085–1088 (1995) and in Bennani et al., "Trans-1,2-diaminocyclohexane Derivatives as Chiral Reagents, Scaffolds, and Ligands for Catalysis—Applications in Asymmetric Synthesis and Molecular Recognition," *Chemical Reviews*, 97:3161–3195 (1997), which are hereby incorporated by reference.

The present invention also relates to a method for making a compound having the formula ("Formula XXXVII"):

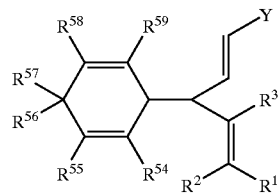

In Formula XXXVII, $R^1$, $R^2$, and $R^3$ are independently selected from H, alkyl, aryl, or vinyl, or $R^1$ and $R^3$, together with the atoms to which they are bonded, form a 5–12 membered ring, such as a cyclohexene ring, or a cyclohexa-1,3-diene ring. The method is particularly well-suited for preparing compounds in which $R^1$ and $R^3$, together with the atoms to which they are bonded, form an aromatic ring, such as a 3,4-dichlorophenyl ring, in which case the compound produced has the formula ("Formula XXXVIII"):

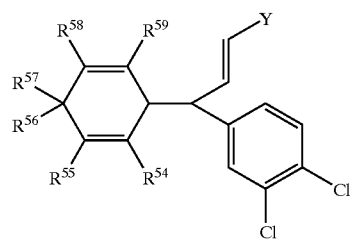

Y is an electron withdrawing group, examples of which include moieties having the formulae: $-C(O)R^{77}$, $-SO_2R^{77}$, and $-P(O)R^{77}R^{77'}$. In these formulae, each of $R^{77}$ and $R^{77'}$ is independently selected from an alkyl group, an aryl group, and an alkoxy group. Preferably, Y has the formula $CO_2R^{12}$ where $R^{12}$ is an alkyl group or an aryl group.

Each of $R^{54}$, $R^{55}$, $R^{56}$, $R^{57}$, $R^{58}$, and $R^{59}$ is independently selected from the group consisting of H, alkyl, aryl, halogen, and alkoxy. Preferably, each of $R^{54}$, $R^{55}$, $R^{56}$, $R^{57}$, $R^{58}$, and $R^{59}$ is hydrogen.

The method includes providing a 1,3-cyclohexadiene having the formula ("Formula XXXIX"):

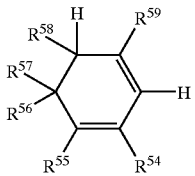

where $R^{54}$, $R^{55}$, $R^{56}$, $R^{57}$, $R^{58}$, and $R^{59}$ are defined as above. The method further includes converting the 1,3-cyclohexadiene with a diazo compound having the formula ("Formula XL"):

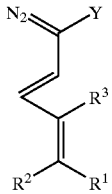

in which Y, $R^1$, $R^2$, and $R^3$ are as defined above. The conversion is carried out in the presence of a bis-transition metal catalyst and under conditions effective to produce the compound.

Suitable bis-transition metal catalysts include, for example, those catalysts set forth above with regard to the method of producing compounds of Formula XXIII.

Typically, the reaction is carried out by mixing the catalyst with the 1,3-cyclohexadiene of Formula XXXIX. In the case where the 1,3-cyclohexadiene of Formula XXXIX is a liquid (e.g., in the case where the compound of Formula XXXIX is 1,3-cyclohexadiene), this can be effected without the use of additional solvent. Alternatively, the mixture can be formed using an inert solvent or a solvent which is significantly less reactive towards the diazo compound of Formula XL than is the compound of Formula XXXIX. Suitable solvents include alkanes, such as hexanes. The solvent is preferably dried prior to use using conventional methods, and the reaction vessel is also preferably dried, such as by flaming or in an oven. The amount of catalyst employed is not critical to the practice of the present invention. Typically, the mole ratio of catalyst to compound of Formula XXXIX is from about 1:10,000 to about 1:20, preferably from about 1:1000 to about 1:100, and more preferably from about 1:500 to about 1:700.

Once the catalyst and compound of Formula XXXIX are mixed, the compound of Formula XL is added, preferably with stirring. Addition can be carried out in a single portion, continuously, or batchwise. Slow, dropwise addition using, for example, a syringe pump is frequently advantageous. The amount of compound of Formula XL added is generally dependent on the amount of compound of Formula XXXIX present in the reaction mixture. Typically the mole ratio of compound of Formula XL to compound of Formula XXXIX is from about 1:10 to about 10:1, preferably from about 1:8 to about 1:1, more preferably from about 1:6 to about 1:4. The addition can be carried out at any suitable temperature from the freezing point to the boiling point of the solvent and/or the compound of Formula XXXIX. Typically, the addition is carried out from about −50° C. to about 60° C., preferably at about room temperature. Generally, higher temperatures favor an undesirable reverse Cope rearrangement in which compounds having Formula XXXVII rearrange to form compounds having the formula ("Formula XLI"):

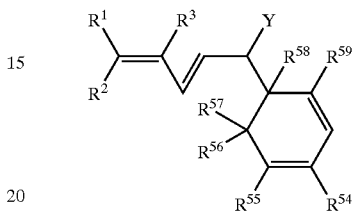

The method is also particularly suitable for making compounds having Formula XXXVII which are substantially diasteriomerically pure, such as, for example, compounds having the formula ("Formula XLII"):

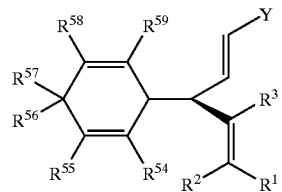

such as compounds having the formula ("Formula XLIII"):

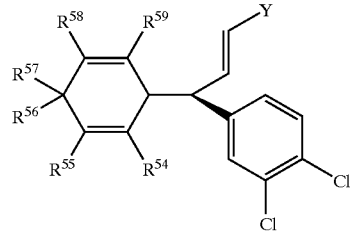

When a substantially diastereomerically selective reaction is desired, the use of a chiral catalyst, preferably one with $D_2$ symmetry, is preferred. For example, by using the S-isomer of compounds having Formulae II, III, IV, V, VI, VII, VIII, IX, and X, as defined and discussed above (particularly where $M^1$ and $M^2$ are Rh or Ru), compounds of Formulae XLII and XLIII which are substantially diasteriomerically pure (e.g., >80% ee, >90% ee, >95% ee, >98% ee, and/or >99% ee) can be prepared.

The present invention also relates to methods for making compounds having the formula ("Formula XLIV"):

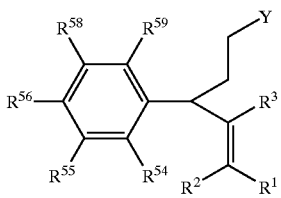

in which $R^1$, $R^2$, $R^3$, $R^{54}$, $R^{55}$, $R^{56}$, $R^{58}$, $R^{59}$, and Y are defined as they were above for the compounds having Formula XXXVII.

The method includes providing a cyclohexadiene derivative having Formula XXXVII wherein $R^{57}$ is H. Preferred cyclohexadiene derivatives which can be used in this reaction are those described above, and they can be conveniently prepared using, for example, the methods disclosed above. Once the cyclohexadiene derivative is provided, it is converted with hydrogenating and oxidizing agents under conditions effective to form the compound of Formula XLIV. The hydrogenation and oxidation reactions can be carried out simultaneously or seuqentially, and, when carried out sequentially, hydrogenation can precede oxidation or oxidation can precede hydrogenation. Suitable hydrogenating agents for use in the present reaction include hydrogen gas in combination with a metal catalyst, such as palladium, preferably palladium on carbon. Other suitable metal catalysts include those set forth in Larock, particularly at pp. 7–12, which is hereby incorporated by reference. Suitable conditions for carrying out such reactions are described, for example, in Larock, particularly at pp. 7–12, and in House, *Modern Synthetic Reactions,* 2nd ed., Menlo Park, Calif.: The Benjamin/Cummings Publishing Company, pp. 1–34 (1972), which are hereby incorporated by reference.

Suitable oxidizing agents for use in the present reaction include those which are generally known to dehydrogenate 1,4-cyclohexadienyl moieties to phenyl moieties, such as 2,3-dicloro-5,6-dicyano-1,4-benzoquinone ("DDQ") and tetrachlorobenzoquinone (a.k.a., chloranil). Other suitable oxidizing agents and suitable conditions for carrying out such reactions are described, for example, in House, *Modern Synthetic Reactions,* 2nd ed., Menlo Park, Calif.: The Benjamin/Cummings Publishing Company, pp. 34–44 (1972), and in Larock, particularly at p. 189, which are hereby incorporated by reference.

The above-described method is particularly useful for making compounds having Formula XLIV in which Y is an alkoxycarbonyl group (e.g., in which Y has the formula —$COOR^{12}$ and $R^{12}$ is an alkyl group) and/or in which $R^1$ and $R^3$, together with the atoms to which they are bonded, form an aromatic ring, such as a 3,4-dichlorophenyl ring. In the latter case, the compound of Formula XLIV has the formula ("Formula XLV"):

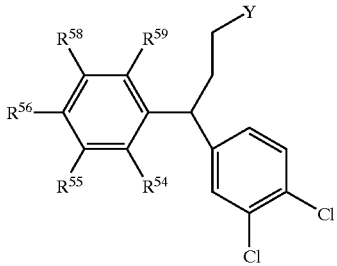

Furthermore, by using a cyclohexadiene having Formula XLII (e.g., a cyclohexadiene having Formula XLIII), sub- stantially diasteriomerically pure compounds of Formula XLIV, such as those having the formula ("Formula XLVI")

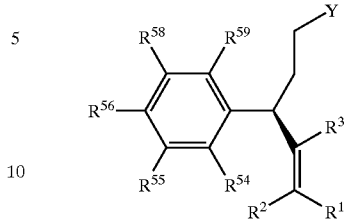

and, more particularly, those having the formula ("Formula XLVII"):

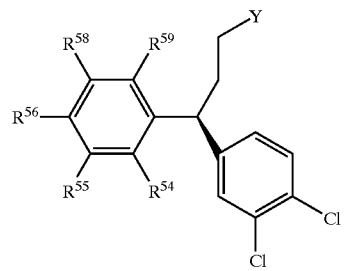

can be prepared.

The present invention, in yet another embodiment thereof, relates to a method for making for preparing a compound having the formula ("Formula XLVIII"):

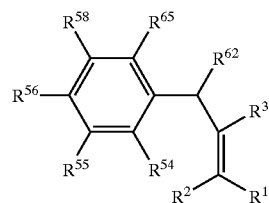

$R^1$, $R^2$, and $R^3$ are independently selected from H, an alkyl group, an aryl group, or a vinyl group, or $R^1$ and $R^3$, together with the atoms to which they are bonded, form a 5–12 membered ring. Preferably, $R^1$ and $R^3$, together with the atoms to which they are bonded, form an aromatic ring, such as a substituted or unsubstituted 1,3-phenylene ring. $R^{54}$, $R^{55}$, $R^{56}$, $R^{58}$, and $R^{65}$ are independently selected from the group consisting of H, alkyl groups, aryl groups, halogen, amino groups (which are meant to include amines that are unsubstituted or mono- or di-substituted with, for example, alkyl or aryl groups), alkoxy groups, hydroxy groups, and acid groups (which are meant to include, carboxylic and sulfonic free acids, acid salts, acid esters, acid amides, and the like). Examples of such compounds include those in which each of $R^{54}$, $R^{55}$, and $R^{56}$ are H and $R^{58}$ is an amino group, such as an unsubstituted amino group. $R^{62}$ represents an alkyl moiety, examples of which include methyl, ethyl, or propyl groups, which can optionally be substituted with, for example, aryl groups (optionally containing a heteroatom) (e.g., pyrid-4-ylmethyl) or amino groups (which are meant to include amines that are unsubstituted or mono- or di-substituted with, for example, alkyl or aryl groups) (e.g., 2-(N,N-diisopropylamino)ethyl). Alternatively, $R^{65}$ and $R^{62}$ together represent the atoms necessary to complete a 5–12 membered, in which case the compound produced has the formula ("Formula XLIX"):

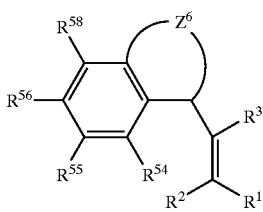

In this formula, $Z^6$ represents, for example, an alkylene group (e.g., a group having the formula —$CH_2CH_2$—, —$CH_2CH_2CH_2$, —$CH(NH_2)CH_2CH_2$—, —$CH_2CH_2CH(NH_2)$—, —$CH_2NRCH_2$—, —$CH_2CH(C_6H_5)CH_2$—, etc.). Specific compounds of Formula XLVIII which can be made using this method include 1,1-diarylalkanes, such as the pharmaceuticals tolterodine and CDP-840, which respectively have the formulae:

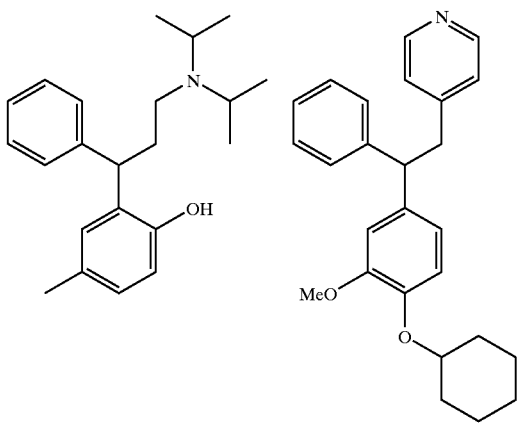

as well as nominfensine and sertraline, which respectively have the formulae:

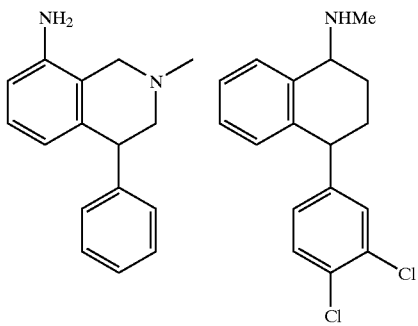

The method includes providing a cyclohexadiene derivative having the formula ("Formula L"):

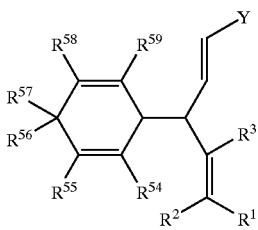

where $R^{57}$ is H, $R^{59}$ is selected from the group consisting of H, alkyl groups, aryl groups, halogens, amino groups, alkoxy groups, hydroxy groups, and acid groups, and Y is an electron withdrawing group. The choice of $R^{59}$ depends upon whether, in the intended product of Formula XLVIII, $R^{65}$ represents an H, an alkyl group, an aryl group, a halogen, an amino group, an alkoxy group, a hydroxy group, or an acid group or whether $R^{65}$ combines with $R^{62}$ to represent a ring structure. In the former case, $R^{59}$ is most conveniently selected so as to be the same as the desired $R^{65}$ group. In the latter case, $R^{59}$ is chosen to be suitably reactive with a cyclizing agent (e.g., $R^{59}$ can be hydrogen). Cyclohexadiene derivatives which can be used in this reaction are those described above, and they can be conveniently prepared using, for example, the methods disclosed above.

Once the cyclohexadiene derivative having Formula L is provided, it is converted with hydrogenating and oxidizing agents under conditions effective to form a phenyl derivative having the formula ("Formula LI"):

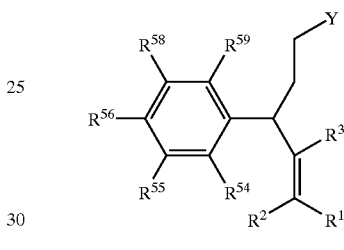

The hydrogenation and oxidation reactions can be carried out simultaneously or sequentially, and, when carried out sequentially, hydrogenation can precede oxidation or oxidation can precede hydrogenation. Suitable hydrogenating and oxidizing agents and methods for their use are described above with regard to to methods for preparing compounds having Formula XLIV.

The phenyl derivative having Formula LI is then converted to the compound having Formula XLVIII. Conditions effective for achieving this conversion depends on the nature of the desired substituents at $R^{62}$ and $R^{65}$. Generally, in the case where $R^{62}$ and $R^{65}$ are discreet moieties (i.e., in the case where $R^{62}$ and $R^{65}$ do not combine to form a ring structure), $R^{59}$ will have been chosen so that no further chemistry is required at that position to obtain the desired $R^{65}$ substituent, and the —$CH_2CH_2Y$ moiety can be converted to the desired $R^{62}$ substituent using conventional methods. In the case where $R^{62}$ and $R^{65}$ combine to form a ring, conventional cyclization chemistry can be employed. For example, in the case where $R^{59}$ is H and $R^{62}$ and $R^{65}$ together represent a —$CH_2CH_2CH_2$— moiety, cyclization can be carried out using, for example, a Friedel-Crafts acylation catalyst, such as those described in Larock, particularly at pp. 1381–1403, which is. hereby incorporated by reference.

The above method for making compounds having Formula XLVIII is illustrated by the following procedure for making sertraline or sertraline congeners having the formula ("Formula LII"):

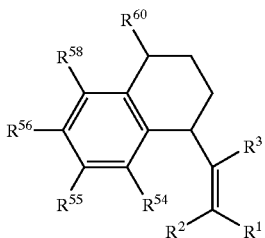

In Formula LII, $R^1$, $R^2$, $R^3$, $R^{54}$, $R^{55}$, $R^{56}$, and $R^{58}$ are defined as they were above with regard to compounds of Formula XXXVII. $R^{60}$ is H. $R^{61}$ can represent a substituted or unsubstituted amine, such as an amine having the formula —$NR^{63}R^{64}$, where each of $R^{63}$ and $R^{64}$ is independently selected from hydrogen, an alkyl group, and an aryl group. Illustratively, $R^{61}$ can be a dialkyl amino group (e.g., $N(CH_3)_2$), a monoalkylamino group (e.g., —$NHCH_2CH_3$), or a monoarylamino group (e.g., —$NH(C_6H_5)$), or $R^{61}$ can represent a cyclic amine moiety, such as a piperidinyl group or a morpholino group. Alternately, $R^{60}$ and $R^{61}$, together with the carbon atom to which they are bonded, can represent a carbonyl (i.e., a C=O) moiety.

The method includes providing a cyclohexadiene derivative having Formula XXXVII in which Y is an electron withdrawing group, such as any one of the electron-withdrawing groups described above, and $R^{57}$ and $R^{59}$ are H. Cyclohexadiene derivatives which can be used in this reaction are those described above. Once the cyclohexadiene derivative is provided, it is converted with hydrogenating, oxidizing, and cyclizing agents under conditions effective to form the compound of Formula LII. The hydrogenation and oxidation reactions can be carried out simultaneously or sequentially, and, when carried out sequentially, hydrogenation can precede oxidation or oxidation can precede hydrogenation. Generally, it is desirable that both hydrogenation and oxidation precede cyclization, that is, that the cyclohexadiene derivative be converted with a hydrogenating agent and an oxidizing agent into a phenyl derivative having the formula ("Formula LIII"):

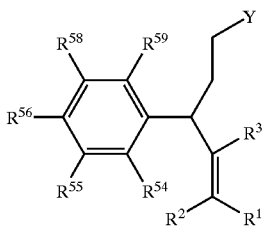

and that the phenyl derivative then be converted with a cyclizing agent under conditions effective to produce the compound.

Suitable hydrogenating and oxidizing agents and methods for their use are described above with regard to to methods for preparing compounds having Formula XLIV. Cyclizing agents suitable for use in the practice of the present invention include acylation catalysts, such as Friedel Crafts acylation catalysts, examples of which include $ClSO_3H$, $AlCl_3$, and other Lewis acids. In the case where Y is an alkoxycarbonyl group, it may be advantageous to convert the alkoxy group to a hydroxy group, prior to treatment with the Friedel Crafts acylation catalyst. This can be done using strong acid, e.g., 6 N HCl, or by any other suitable method. The immediate product of such a cyclization is a tetralone having the formula:

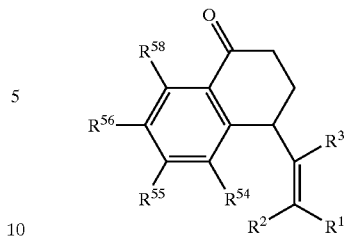

which can be readily converted to compounds having Formula LII by methods known to those skilled in the art, such as the reductive amination method set forth in Corey, which is hereby incorporated by reference.

The above-described method is particularly useful for making compounds having Formula LII in which Y is an alkoxycarbonyl group (e.g., in which Y has the formula —$COOR^{12}$ and $R^{12}$ is an alkyl group) and/or in which $R^1$ and $R^3$, together with the atoms to which they are bonded, form an aromatic ring, such as a 3,4-dichlorophenyl ring, in which case the compound of Formula LII has the formula ("Formula LIV"):

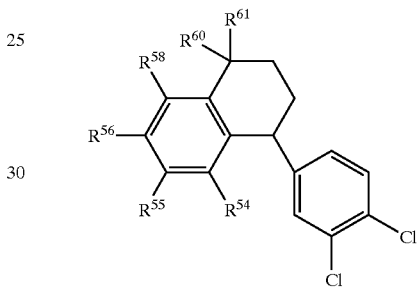

Furthermore, by using a cyclohexadiene having Formula XLII (e.g., a cyclohexadiene having Formula XLIII), substantially diasteriomerically pure compounds of Formula LII, such as those having the formula ("Formula LV"):

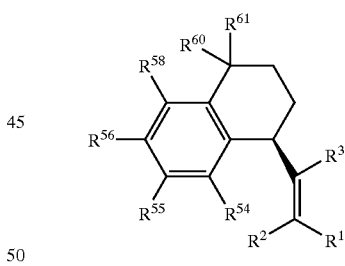

and, more particularly, those having the formula ("Formula LVI"):

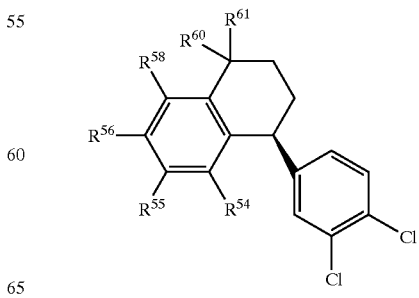

can be prepared.

The present invention is further illustrated by the following non-limiting examples.

set forth in this scheme are described, below, in Examples 2–6.

SCHEME I

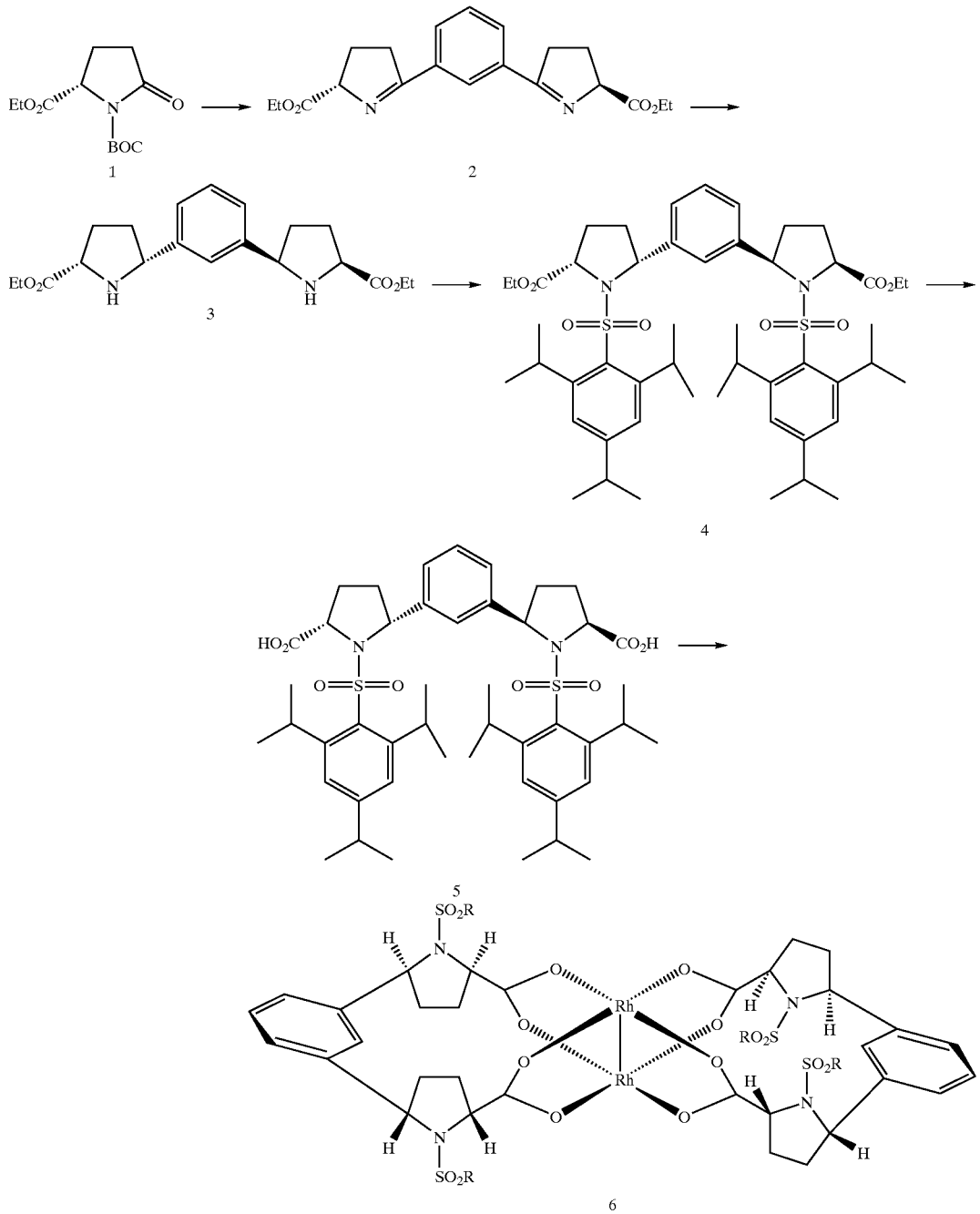

EXAMPLES

Example 1
Synthetic Scheme for the Preparation of Dirhodium Bis[bridged-di(S-2,4,6-triisopropylphenylsulfonylprolinate)]

Dirhodium bis[bridged-di(S-2,4,6-triisopropylphenylsulfonylprolinate)] was prepared using the following general reaction Scheme I, in which R represents a 2,4,6-triisopropylphenyl group. Details for each step

Example 2
Preparation of Imine 2

To a −78° C. solution of 1,3-diiodobenzene (3.431 g, 10.4 mmol) in THF (100 ml) was added 1.7 M t-butyl lithium (25.1 ml, 42.6 mmol, 4.1 equiv). The mixture was stirred at −78° C. for 0.5 hours and then allowed to warm to room temperature over 1 hour. The mixture was then cooled to −78° C. again and then added to a −78° C. solution of S-N-BOC-pyroglutamic ethylester (1) (13.62 g, 62.4 mmol, 6.0 equiv) in THF (75 ml). The resulting mixture was stirred at −78° C. for 1 hour and then stirred at room termperature for 20 hours. The reaction mixture was poured into water (300 ml), and extracted with ethyl acetate. The organic layer was separated and dried with $MgSO_4$, and the solvent was removed to produce a residue.

The residue was dissolved in dichloromethane (60 ml). To this was added TFA (48.1 ml, 0.624 mol), and the resulting mixture was stirred at room temperature for 20 hours. The solvent was then removed, and the residue was redissolved in dichloromethane and then extracted four times with saturated bicarbonate, twice with water, and then with brine. The organic layer was separated and dried with $MgSO_4$, and solvent was removed. The resulting residue was purified by chromatography on silica using EtOAc/hexanes (5:4) to give 1.3827 g of imine 2 as an oil (37%): TLC $R_f$ 0.33 (EtOAc/hexanes (70:30)); $[\alpha]^{25}D=109°$ (c 1.358, $CHCl_3$); IR (NaCl) 2981, 1738, 1623, 1576 $cm^{-1}$; $^1H$ NMR (400 MHz, $CDCl_3$) δ8.31 (s, 1H), 7.95 (d 2H), 7.43 (t, 1H), 4.88 (dd, 2H, J=7.6, 7.2 Hz), 4.21 (q, 4H, J=7.6 Hz), 3.22–3.08 (m, 2H), 3.04–2.90 (m, 2H), 2.40–2.27 (m, 2H), 2.27–2.13 (m, 2H), 1.29 (t, 6H, J=7.2 Hz); $^{13}C$ NMR (75 MHz, $CDCl_3$) δ174.7, 171.9, 133.3, 129.5, 127.7, 126.7, 73.8, 60.1, 34.6, 25.6, 13.3. HRMS (EI) calcd for $C_{20}H_{24}N_2O_4$, 356.1736, found 356.1718.

Example 3
Preparation of Diamine 3

Imine 2 (2.4236 g, 6.80 mmol) was hydrogenated at 55 psi of $H_2$, with $PtO_2$ (6 mg/mmol of substrate) in ethanol (6 ml/mmol of substrate). The reaction was agitated for 25 hours and then filtered through a plug of celite. The solvent was removed under reduced pressure, and the residue was purified by chromatography on silica using EtOAc/hexanes (2:1 w/5% triethylamine) to give 2.196 g of diamine 3 as an oil (90%): TLC $R_f$ 0.31 (EtOAc/hexanes (2:1 w/5% triethylamine)); $[\alpha]^{24}D=11°$ (c 3.794, $CHCl_3$); IR (NaCl) 3356, 2983, 2908, 2876, 1742, 1731, 1609, 1454, 1380 $cm^{-1}$; $^1H$ NMR (300 MHz, $CDCl_3$) δ7.45 (s, 1H), 7.40–7.25 (m, 3H), 4.30–4.10 (m, 6H), 3.90 (dd, 2H, J=8.4, 8.1 Hz), 2.42 (s, 2H), 2.30–2.05 (m, 6H), 1.92–1.60 (m, 2H), 1.30 (t, 6H, J=7.5 Hz); $^{13}C$ NMR (75 MHz, $CDCl_3$) δ174.8, 143.2, 128.3, 125.2, 125.1, 63.2, 60.6. 59.7, 33.8, 30.2, 13.9; HRMS (EI) calcd for $C_{17}H_{23}N_2O_2$(m-COOEt), 287.1757, found 287.1723.

Example 4
Preparation of Bridged di(ethyl S-2,4,6-triiso-propylphenylsulfonylprolinate) 4

Diamine 3 (1.4 g, 3.95 mmol) and potassium carbonate (2.2 g, 15.8 mmol, 4.0 equiv) were stirred in acetone (40 ml). Then, 2,4,6-triisopropylbenzenesulfonyl chloride (3.6 g, 11.8 mmol, 3.0 equiv) was added. After the resulting reaction mixture was stirred for four (4) days at room temperature, a second portion of acetone (100 ml) was added. The mixture was filtered, and the solvent was removed under reduced pressure. The residue was purified by chromatography on silica using EtOAc/hexanes (1:9) to give 2.1 g of bridged di(ethyl S-2,4,6-triiso-propylphenylsulfonylprolinate) ("diTiPBSP-COOEt") 4 as a white solid (mp 57–59° C.) (59%): TLC $R_f$ 0.16 (EtOAc/Hexanes (10:90)); $[\alpha]^{23}D=-21°$ (c 2.188, $CHCl_3$); IR (NaCl) 2963, 2868, 2263, 1753, 1600, 1563, 1463, 1316, 1153 $cm^{-1}$; $^1H$ NMR (300 MHz, $CDCl_3$) δ7.60 (d, 2H, J=7.8 Hz), 7.28–7.20 (m, 2H), 7.07 (s, 4H), 5.13 (t, 2H, J=6.3 Hz), 4.53 (dd, 2G, J=7.2, 4.8, Hz), 4.16–3.82 (m, 8H), 2.84 (sept, 2H, J=6.9 Hz), 2.50–2.00 (m, 8H), 1.19 (d, 12H, J=6.9 Hz), 1.18 (d, 12H, J=6.3 Hz), 1.12 (d, 12H, J=6.9 Hz), 1.01 (t, 6H, J=7.1 Hz); $^{13}C$ NMR (75 MHz, $CDCl_3$) δ171.8, 153.3, 151.8, 151.7, 141.3, 130.4, 127.8, 126.8, 126.1, 123.5, 63.8, 61.0, 60.7, 35.4, 33.9, 29.9, 29.2, 24.8, 24.5, 23.3, 13.7; Anal. Calcd for $C_{50}H_{72}N_2O_8S_2$: C, 67.23; H, 8.12; N, 3.13. Found: C, 66.99; H, 8.19; N, 3.08.

Example 5
Preparation of Bridged di(S-2,4,6-triiso-propylphenylsulfonylproline) 5 diTiPBSP-COOEt 4 (2.1 g, 2.33 mmol) was dissolved in THF (12 ml), and, then, $H_2O$ (6 ml), $LiOH.H_2O$ (323 mg, 7.69 mmol, 3.3 equiv), and ethanol (6 ml) were added. The reaction was stirred at room temperature for five (5) hours, and, then, it was acidified with 0.5 N HCl to a pH of 2. The acidified mixture was extracted with dichloromethane and separated. The organic layer was dried with $Na_2SO_4$, and the solvent was removed to give a solid. The solid was purified by recyrstalization with chloroform/hexanes to give 2.07 g of bridged di(S-2,4,6-triiso-propylphenylsulfonylproline) ("diTiPBSP-COOH") 5 as a white solid (mp 86–88° C.) (Quantitative): $[\alpha]^{25}D=116°$ (c 1.256, $CHCl_3$); IR (NaCl) 3062, 2961, 2929, 2876, 2759, 2648, 2569, 2261, 1726, 1604, 1561, 1460, 1434, 1365, 1317, 1248, 1158 $cm^{-1}$; $^1H$ NMR (300 MHz, $CDCl_3$) δ11.07 (s, 2H), 7.70 (s, 1H), 7.20–6.95 (m, 5H), 6.81 (s, 2H), 4.93 (t, 2H, J=6.3 Hz), 4.73 (t, 2H, J=6.5 Hz), 3.98 (sept, 4H, J=6.6 Hz), 2.82 (sept, 2H, 6.6 Hz), 2.60–2.00 (m, 8H), 1.18 (d, 12H, J=6.6 Hz), 1.12 (d, 12H, J=6.3 Hz), 0.99 (d, 12H, J=6.6 Hz); $^{13}C$ NMR (75 MHz, $CDCl_3$) 5 178.3, 153.6, 151.7, 141.1, 129.9, 127.6, 126.7, 126.4, 123.5, 64.2, 60.1, 34.1, 33.9, 30.4, 29.2, 29.1, 24.7, 24.6, 23.3; Anal Calcd. for $C_{46}H_{64}N_2O_8S_2$: C, 66.00; H, 7.71; N, 3.35. Found: C, 65.71; H, 7.93; N, 3.22.

Example 6
Preparation of Dirhodium Bis [bridged-di(S-2,4,6-triisopropylphenylsulfonylprolinate)] 6 diTiPBSP-COOH 5 (1.00 g, 1.2 mmol) and rhodium acetate (240 mg, 0.54 mmol) were dissolved in chlorobenzene (35 ml). The solution was refluxed through a soxhlet extractor containing calcium carbonate for 72 hours. The solution was then cooled, and the solvent was removed under reduced pressure. The residue was purified by chromatography on silica using EtOAc/hexanes (1:9) to give 484 mg of dirhodium bis[bridged-di(S-2,4,6-triisopropylphenyl-sulfonylprolinate)] as a green solid (48%): TLC $R_f$ 0.18 (EtOAc/hexanes (10:90)); IR (NaCl) 2966, 2929, 2871, 1603, 1417, 1321, 1161 $cm^{-1}$; $^1H$ NMR (400 MHz, $CDCl_3$) δ7.10 (s, 8H), 6.97 (t, 2H, J=7.4 Hz), 6.81 (d, 4H, J=8.4 Hz), 6.80 (s, 2H), 4.63 (t, 4H, J=8.2 Hz), 4.39 (d, 4H J=7.6 Hz), 3.47 (sept, 8H, J=6.4 Hz), 2.96 (sept, 4H, J=6.8 Hz), 2.41 (dd, 4H, 12.2, 6.0 Hz), 2.24–2.14 (m, 4H), 2.14–2.00 (m, 4H), 1.76–1.63 (m, 4H), 1.31 (d, 12H, J=6.8 Hz), 1.29 (d, 12H, J=6.8 Hz), 1.05 (d, 24H, J=6.8 Hz), 0.94 (d, 24H, J=6.0 Hz); $^{13}C$ NMR (75 MHz, $CDCl_3$) δ190.5, 153.1, 151.4, 141.6, 130.5, 127.1, 127.0, 124.7, 123.6, 64.7, 62.3, 34.9, 34.0, 29.3, 27.8, 25.0, 24.6, 23.5; HRMS (FAB) calcd for $C_{92}H_{125}N_4O_{16}S_4Rh_2$ 1875.6084, found 1875.6076.

Example 7
Regio-, Diastereo-, and Enantio-selective C—H Insertions of Aryldiazoacetates Into Cyclic N-BOC Protected Amines This example demonstrates that highly regio-diastereo- and enantioselective C—H insertions of aryldiazoacetates into cyclic N-BOC protected amines can be achieved by using dirhodium tetrakis(S-4-dodecylphenylsulfonylprolinate) ("$Rh_2(S-DOSP)_4$"), which has the following formula:

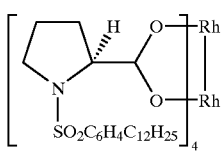

and by using dirhodium bis[bridged-di(S-4-t-butylphenylsulfonylprolinate)] ("Rh$_2$[bridged(S-TBSP)$_2$]$_2$"), which has the following formula:

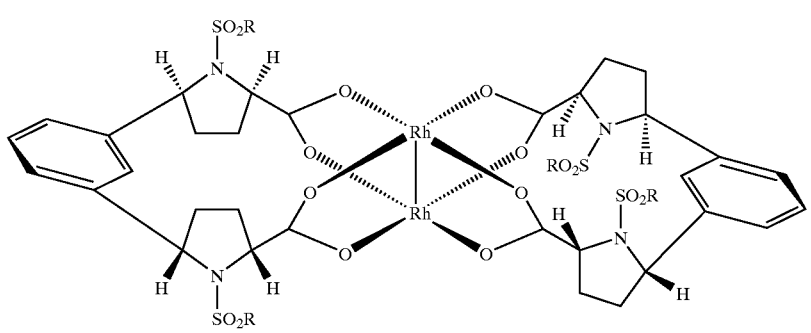

in which each R represents a 4-t-butylphenyl group. Rh$_2$(S-DOSP)$_4$ was purchased commercially from Aldich, and Rh$_2$[bridged(S-TBSP)$_2$]$_2$ was made using the procedures set forth in Examples 1–6, above, except that diamine 3 was reacted with 4-t-butylbenzenesulfonyl chloride instead of 2,4,6-triisopropylbenzenesulfonyl chloride.

The highly regio-, diastereo-, and enantioselective C—H insertion of aryldiazoacetates into cyclic N-BOC protected amines was carried out using Rh$_2$(S-DOSP)$_4$ in the following reaction Scheme II:

SCHEME II

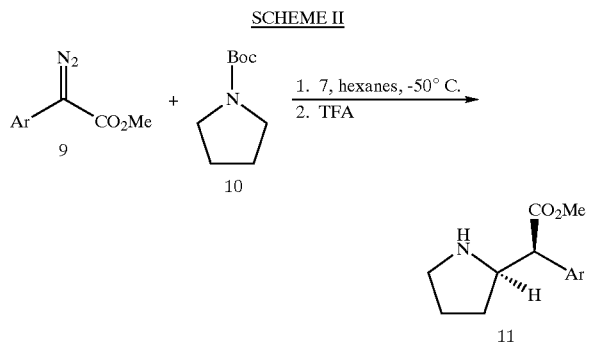

Briefly, methyl phenyldiazoacetate (9, Ar=phenyl) was prepared from methyl diazoacetate by the general method set forth in Davies et al., "Direct Synthesis of Furans From Rhodium(III) Stabilized Carbenoids With Alkenes," *Org. Synth.*, 70:92–99 (1991), which is hereby incorporated by reference. To 5 ml of hexanes were added of N-BOC pyrrolidine (10) (0.351 g, 2 mmol, 2 equiv) and Rh$_2$(S-DOSP)$_4$ (0.019 g, 0.01 mmol, 0.01 equiv). The mixture was chilled to −50° C., and methyl phenyldiazoacetate (0.176 g, 1 mmol, 1 equiv) in 10 ml hexanes was added. The mixture was stirred for 12 hours and then warmed slowly to room temperature. The solvent and excess N-tert-butyl-pyrrolidine carboxylate were removed on a rotary evaporator and by kugelrohr distillation. The crude product was treated with TFA (10 equiv) at room temperature for one hour and was thrice extracted with water. The aqueous phase was basified to pH 10–11 with NaHCO$_3$ and thrice extracted with methylene chloride. The combined organic layers were dried with MgSO$_4$ and concentrated to give the free amine (11 (Ar=phenyl)) in 96:4 dr (by $^1$H-NMR). To calculate yield, the free amine (11 (Ar=phenyl)) was converted to its hydrochloride salt by dissolving the free amine in ethyl ether (5 ml), adding an excess of a 1 M HCl/diethyl ether solution, filtering the resulting precipitate, washing the collected solid with diethyl ether, and drying the resulting white solid. The overall yield was 183 mg or 72%.

In like manner, the above reaction was repeated for other methyl aryldiazoacetates, and the results are presented in Table I, below:

TABLE I

|   | Ar | yield, % | ee, % | de, % |
|---|---|---|---|---|
| a | Ph | 72 | 94 | 92 |
| b | p-Cl-Ph | 70 | 94 | 94 |
| c | p-Me-Ph | 67 | 93 | 94 |
| d | 2-Naphthyl | 49 | 93 | 92 |

In Table I, the diastereoselectivity of the formation of 11 was determined from the $^1$H NMR of the crude amine after extraction and removal of solvent. The yields for 11a and 11c–11e represent the amounts of crystalline hydrochloride salt that was obtained after treating the crude amine with ethereal HCl. The yield of 11b represents the pure amine after purification by column chromatography. The enantioselectivity was determined by conversion of the crude amine to its trifluoroacetamide derivative followed by chiral HPLC or GC analysis. The relative stereochemistry of 11c was readily determined by converting 11c to a fused β-lactam in which the cis arrangement of the 2 protons in the β-lactam ring was assigned on the basis of a distinctive coupling (J=5.1 Hz) and nOe experiments (Coulton et al., *Chem Soc. Perkin Trans. I*, 1998:1193–1202, which is hereby incorporated by reference). The absolute stereochemistry of 11a was determined to be (2S, 2'R) using the Mosher amide method described in Hoye et al., *Org. Chem.*, 61:8489–8495 (1996), which is hereby incorporated by reference.

The next issue that was examined was whether a second C—H insertion was a feasible process. The reactions and results are summarized in Scheme III, below:

SCHEME III

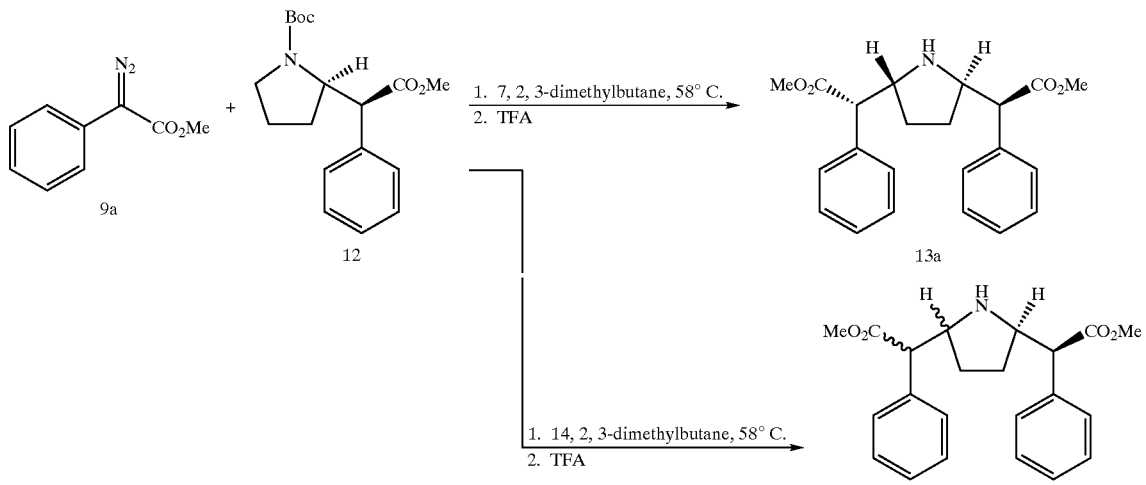

The reactions were carried out on enantiomerically pure 12 which was obtained from 11a that was first recrystallized as its hydrochloride salt to obtain enantiomerically pure material and then treated with $(BOC)_2O$. Reaction of 12 with the phenyldiazoacetate 9a (4 equiv) using $Rh_2(S-DOSP)_4$ as catalyst in 2,3-dimethylbutane as solvent resulted in the formation of 13a in 93% yield. The compound was shown to be $C_2$-symmetric because, in the $^{13}C$ NMR, only 9 signals were apparent. Since the compound is chiral, this rules out the meso diastereomer. In contrast, reaction of 12 with excess 9a using $Rh_2(R-DOSP)_4$ (sometimes denoted "14" hereinafter) as the catalyst, resulted in the formation of mixture of diastereomers and/or regioisomers that were not resolvable.

Further experimentation demonstrated that the $C_2$-symmetric amines could be formed in a single step, as shown in Scheme IV, below:

SCHEME IV

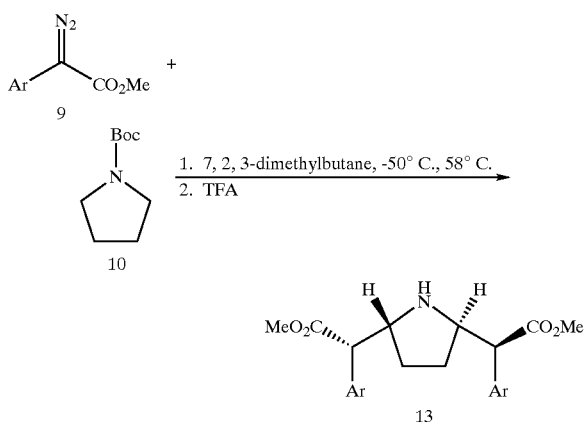

Briefly, $Rh_2(S-DOSP)_4$-catalyzed decomposition of 9a (1.5 equiv) at −50° C. in the presence of N-BOC-pyrrolidine 10 followed by warming the reaction to 58° C. and addition of a further 4.5 equiv of 9a generated the $C_2$-symmetric amine 13a in 78% yield and 97% ee. Similar bis C—H insertion reactions were carried out with aryldiazoacetates 9b–9e to produce the amines 13b–13e, as summarized in Table II, below:

TABLE II

|   | Ar | yield, % | ee, % |
|---|---|---|---|
| a | Ph | 78 | 97 |
| b | p-Cl-Ph | 50 | 96 |
| c | p-Me-Ph | 51 | 96 |
| d | 2-Naphthyl | 62 | 88 |
| e | p-MeO-Ph | 40 | 97 |

These amines are appropriately functionalized for further conversion by ester reduction or Grignard addition to highly functionalized and potentially useful $C_2$-symmetric bases.

Experiments were performed to determine whether it would be feasible to carry out a similar reaction using N-BOC-piperidine, which would provide a direct synthesis of threo-methylphenidate (RITALIN™). The experiments and results are summarized in Scheme V and Table III, below:

SCHEME V

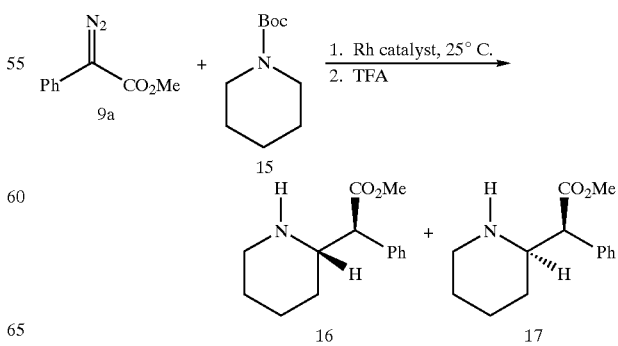

TABLE III

| Rh catalyst | equiv of 15 | 16 + 17 yield, % | 16:17 ratio | 16 ee, % | 17 ee, % |
|---|---|---|---|---|---|
| 7 | 4.0 | 49 | 43:57 | 34 (2S) | 81 (2S) |
| 7 | 0.25 | 86 | 50:50 | 25 (2S) | 79 (2S) |
| 8 | 0.25 | 73 | 71:29 | 86 (2R) | 65 (2R) |

As shown above in Scheme V and Table III, $Rh_2(S\text{-DOSP})_4$ 7 catalyzed decomposition of methyl phenyldiazoacetate 9a in the presence of N-BOC-piperidine (15, 4 equiv) in 2,3-dimethylbutane at room temperature followed by treatment with trifluoroacetic acid resulted in the formation of a mixture of threo and erythro methyphenidate, 16 and 17, in 49% yield. However, the threo isomer 16 was the minor diastereomer and was formed in only 34% ee. The combined yield of 16 and 17 was improved to 86% by using the N-BOC-peperidine as the limiting reactant. This result is different to what was observed with N-BOC-pyrrolidine, which gave bis C—H insertion when an excess of phenyldiazoacetate was used. A major improvement in enantioselectivity and diastereoselectivity was achieved by carrying out the reaction with the $Rh_2[bridged(S\text{-TBSP})_2]_2$ 8 catalyst. The ratio of 16:17 (73% yield) was improved to 2.5:1 and (2R, 2'R)-threo isomer 16 was formed in 86% ee and 52% isolated yield. As shown in Table III, $Rh_2[bridged(S\text{-TBSP})_2]_2$ 8 results in opposite asymmetric induction to $Rh_2(S\text{-DOSP})_4$ 7, and, in the reaction of 9a and 15 catalyzed by 8, the biologically active enantiomer of threo-methylphenidate is formed.

The erythro diastereomer of methylphenidate 17 was produced by carrying out the reaction with dihydropyridine 18 as illustrated in Scheme Va, below:

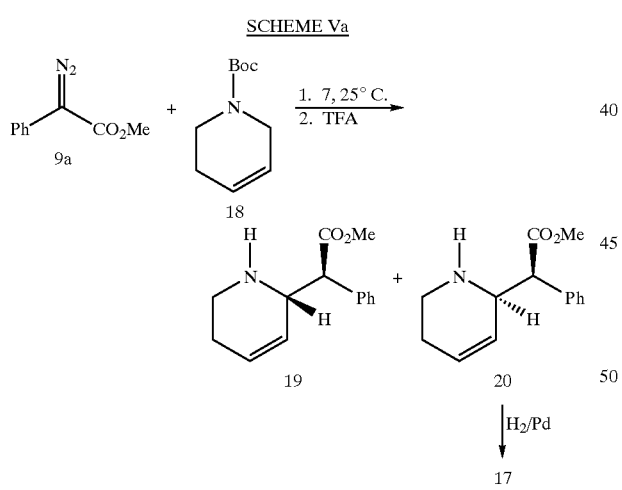

Refering to Scheme Va, $Rh_2(S\text{-DOSP})_4$ catalyzed decomposition of 9a in the presence of 18 (4 equiv) in 2,3-dimethylbutane at room temperature followed by treatment with TFA resulted in a 63% yield of C—H insertion products 19 and 20. The erythro diastereomer 20 was the major diastereomer (62% de) and was isolated in 53% yield and 80% ee. Determination of the relative and absolute stereochemistry of 20 as (2S, 2'R) was readily achieved by converting 20 to erythro-methylphenidate 17 by catalytic hydrogenation using hydrogen and a paladium hydrogenation catalyst.

Example 8
Intermolecular C—H Insertion Reactions Between Allyl Silyl Ethers and Methyl Aryldiazoacetates This example describes further studies to explore the scope of the asymmetric intermolecular C—H insertion with particular emphasis on the chemoselectivity and diastereoselectivity of the reaction.

Simple allyloxy substrates and $Rh_2[(\pm)\text{-DOSP}]_4$ (sometimes denoted "21" hereinafter) as catalyst were initially used to study the selectivity of the C—H insertions. These reactions are summarized in Scheme VI, below:

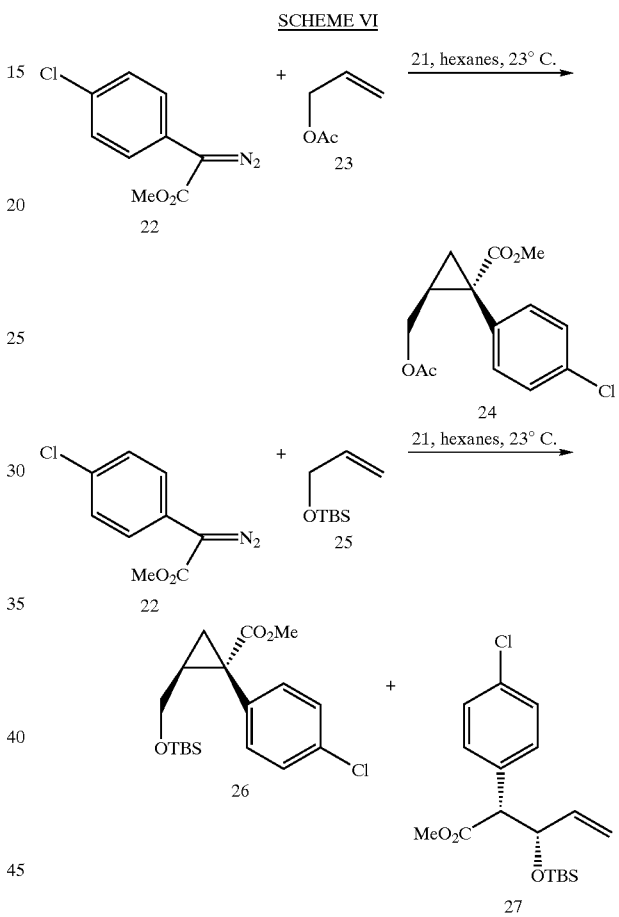

In the case of the reaction of 4-chlorophenyldiazoacetate 22 with allyl acetate 23 (2 equiv) at room temperature, cyclopropanation was the exclusive reaction, and 24 was formed in 75% yield. In contrast, in the reaction of 22 with allyl silyl ether, the C—H insertion product 27 was the major product, and, remarkably, it was formed in >94% de. Interestingly, it appears that the $Rh_2[(\pm)\text{-DOSP}]_4$ catalyst has a major influence on the product distribution because, when the reaction is carried out with dirhodium tetraoctanoate, $Rh_2(OOct)_4$, as catalyst, the ratio of cyclopropane 26 to C—H insertion product 27 was 2.5:1. No reaction occurred with the dirhodium tetracarboxaminde catalyst, $Rh_2(R\text{-MEPY})_4$ (see Davies, which is hereby incorporated by reference), under these reaction conditions.

The preferential formation of the C—H insertion product 27 is an unprecedented result, because mono-substituted alkenes generally undergo cyclopropanation in high yield on reaction with methyl phenyldiazoacetate. On repeating the reaction with more highly substituted allyl ethers 28, cyclopropanation could be fully eliminated. This is illustrated in Scheme VII and Table IV below:

SCHEME VII

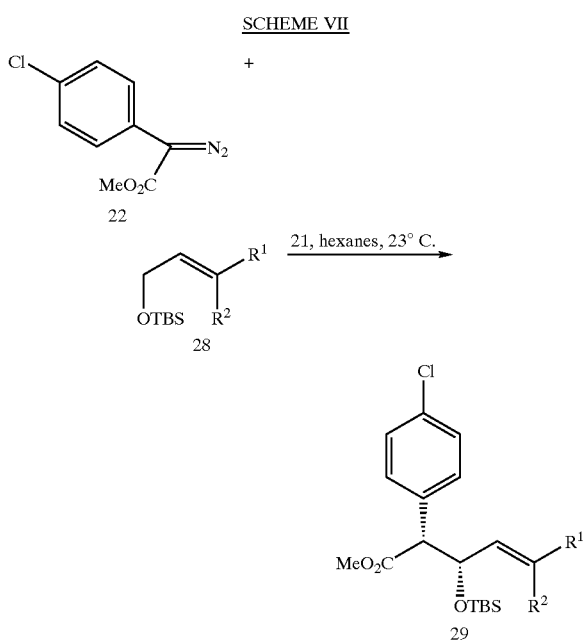

TABLE IV

|   | R¹ | R² | yield, % | de, % |
|---|---|---|---|---|
| a | H | Me | 48 | 66 |
| b | Me | Me | 44 | 70 |
| c | Me | H | 72 | >94 |

However, the diastereoselectivity of the C—H insertion was dependent on the allyl ether substitution pattern. With the trans-dissubstituted or trisubstituted allyl ethers 28a and 28b, the C—H insertion products 29a and 29b were formed with a syn/anti ratio of about 7:1. However, with the trans disubstituted allyl ether 28c, the C—H insertion product 29c was formed in 72% yield and >94% de.

The steric influences on the C—H insertion versus cyclopropanation can be seen in the reaction with 2-methylpropenyl silyl ether in Scheme VIII, below:

SCHEME VIII

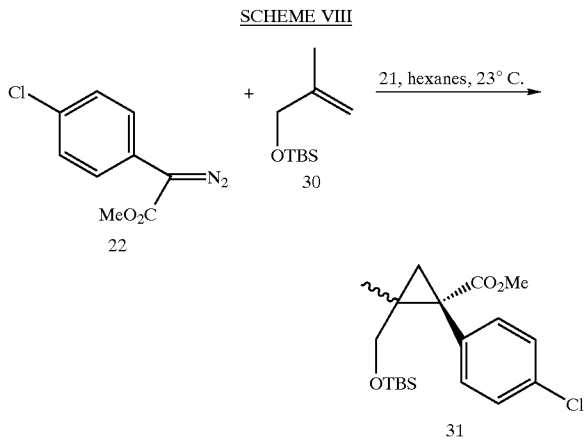

Here, reaction with the 2-methylpropenyl silyl ether 30 results in the formation of the cyclproane 31 without any evidence showing formation of the C—H insertion product. It is believed that, because the aryldiazoacetate cyclopropanation is nonsynchronous, the silyl ether 30 has an accessible vinyl terminus for cyclopropanation, while the methyl substituent in 30 is presumably interfering with the C—H insertion.

Having thus discovered that the trans allyl silyl ether is a promising substrate for diastereoselective C—H insertion, the study was extended to explore the issue of asymmetric induction within this system. $Rh_2(S\text{-}DOSP)_4$ 7 catalyzed decomposition of 22 in the presence of a series of allyl silyl ethers was carried out using the following procedure. A flame dried 50 ml round bottom flask equipped with a magnetic stir bar and a rubber septum was charged with silyl ether (1.5 mmol), $Rh_2(S\text{-}DOSP)_4$ (14 mg, $7.5 \times 10^{-3}$ mmol), and dry hexane (0.5 ml), and the mixture was stirred under argon at room temperature to give a green solution. A 10 ml gastight syringe was charged with p-chlorophenyldiazoacetate (0.75 mmol) in dry hexane (7.5 ml) to give a 0.10 M diazo solution. Addition via syringe pump was initiated at a rate of 7.5 ml/h (1 h addition time), and the green color of the reaction mixture was maintained during the entire addition. After the diazo addition was complete, the reaction mixture was allowed to stir for an additional hour, and then the solvent and excess silyl ether were removed under reduced pressure. The residue was purified by flash chromatography on silica gel using 96:4 petroleum ether:ether to give the product as a clear oil. The reaction is set forth in Scheme IX, and the results are summarized in Table V below:

SCHEME IX

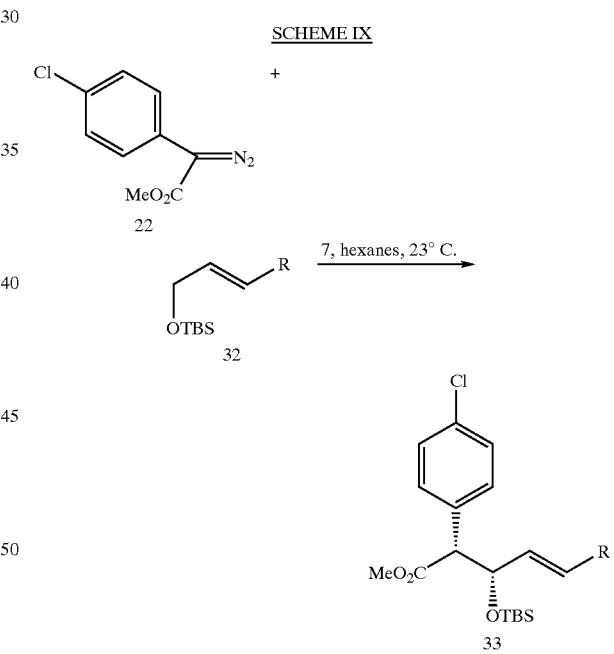

TABLE IV

| Product | R | yield, % | de, % | de, % |
|---|---|---|---|---|
| 33a | Me | 72 | >94 | 80 |
| 33b | Ph | 55 | >94 | 85 |
| 33c | CH=CH₂ | 41 | >94 | 74 |
| 33d | H | 35 | >94 | 90 |

In all instances, the diastereocontrol was >94% de favoring the syn isomer, and the enantioselectivity ranged from 74–90% ee.

In order to determine the absolute stereochemistry of the C—H insertion product, the Rh$_2$(S-DOSP)$_4$ catalyzed reaction of methyl phenyldiazoacetate 34 with allyl silyl ether 35 was examined. The reaction is set forth in Scheme X, below:

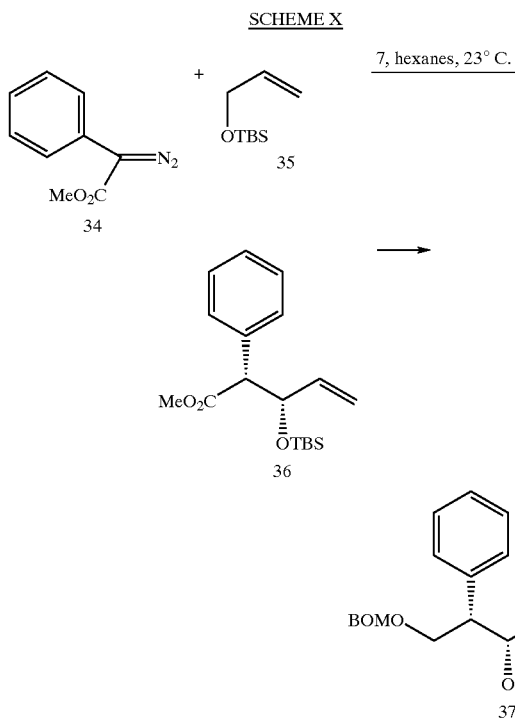

The reaction resulted in the formation of syn isomer 36 as the major product in 52% yield (2.8:1 ratio of 36 to cyclopropane product) and 92% ee. Lithium aluminum hydride reduction of 36, followed by conversion of the alcohol to its t-butoxymethoxy derivative and silyl deprotection gave 37. The optical rotation of 37 was compared with the value given in Guanti et al., *Tetrahedron*, 51:10343–10360 (1995), which is hereby incorporated by reference. The absolute stereochemistries of other C—H insertion products are tentatively assigned assuming a similar mode of asymmetric induction for all the substrates.

In summary, these studies, demonstrate that the intermolecular C—H insertions of carbenoids derived from aryl diazoacetates is a practical method for the asymmetric synthesis of products that are typically derived from an aldol reaction. The reaction proceeds with good chemo- and diastereoselectivity, and by using Rh$_2$(R-DOSP)$_4$ as catalyst, reasonably high levels of asymmetric induction can be obtained. One particularly attractive feature of this chemistry is the low molar equivalent of catalyst that is required.

Example 9

Catalytic Asymmetric Synthesis of Diarylacetates and 4,4-dirarylbutanoates

This example illustrates a method for the synthesizing diarylacetates and 4,4-diarylbutanoates using asymmetric carbenoid transformations. The practical utility of this methodology is demonstrated by a short formal synthesis of the antidepressant (−)-sertraline, which has the formula:

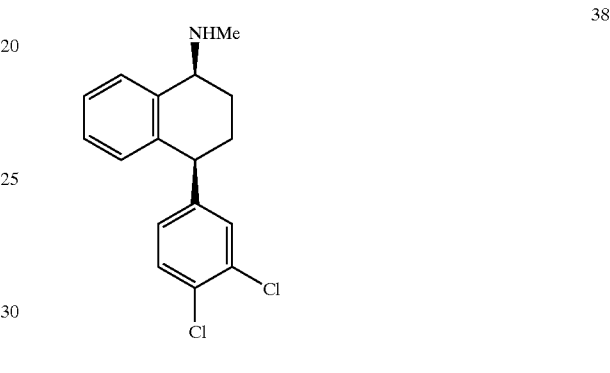

Briefly, the method involves reacting methyl phenyldiazoacetate 39 with 1,3-cyclohexadiene 40 in the presence of Rh$_2$(S-DOSP)$_4$ 7, and the reaction preferentially formed the C—H insertion product 41 rather than the cyclopropanated product 42. The C—H insertion product 42 was formed as an inseparable 4:1 mixture of diastereomers, and, so, in order to determine the extent of the asymmetric induction, 42 was reduced to the known cyclohexane 43, which was formed in 92% ee (R-configuration). An even more effective C—H insertion was achieved on reaction of 39 with 1,4-cyclohexadiene 44, as this resulted in the formation of the C—H insertion product 45 with very little occurrence of the cyclopropanation reaction. The absolute stereochemisty of 45 was determined to be R by reduction of 45 to the cyclohexane 43 (80% overall yield from 39 with a 91% ee). These reactions are summarized in Scheme XI, below:

SCHEME XI

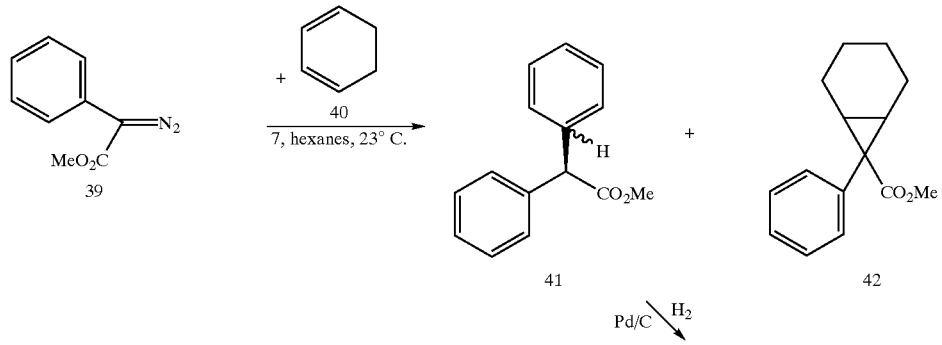

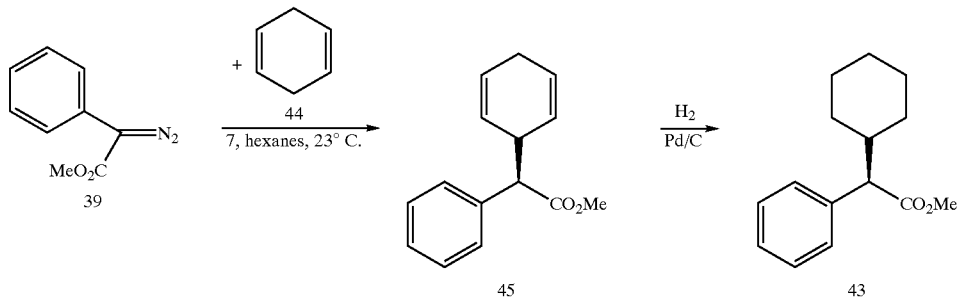

The reaction with 1,4-cyclohexadiene could be carried out with a range of aryldiazoacetates 46 as illustrated in Scheme XII and Table VI, below:

SCHEME XII

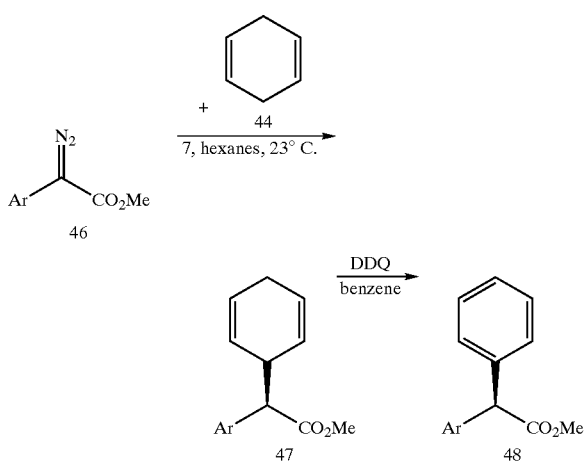

TABLE VI

|   | Ar | yield 47, % | ee 47, % | yield 48, % | ee 48, % |
|---|---|---|---|---|---|
| a | p-Cl-Ph | 84 | 95 | 86 | 95 |
| b | p-Me-Ph | 84 | 94 | 89 | 94 |
| c | p-MeO-Ph | 69 | 93 | 87 | 93 |
| d | 2-naphthyl | 64 | 92 | 88 | 92 |

In each case, the C—H insertion product 47 was produced in >90% ee. Furthermore, 47 could be readily oxidized by DDQ to the diarylacetate 48 without racemization. The absolute stereochemistry for 47 and 48 is tentatively assigned on the assumption the asymmetric induction would parallel that observed in the formation of 45.

The new strategy to 4,4-diarylbutanoates was discovered on attempting the C—H insertion reaction with the phenylvinyldiazoacetate 49. Reaction of 49 with 1,3-cyclohexadiene 40 did not result in the formation of the expected C—H insertion product. Instead, the 1,4-cyclohexadiene 50 was formed in 63% yield and 98% ee. A side product in this reaction is the cyclopropanation/Cope rearrangement product 51, as shown in Scheme XIII, below:

SCHEME XIII

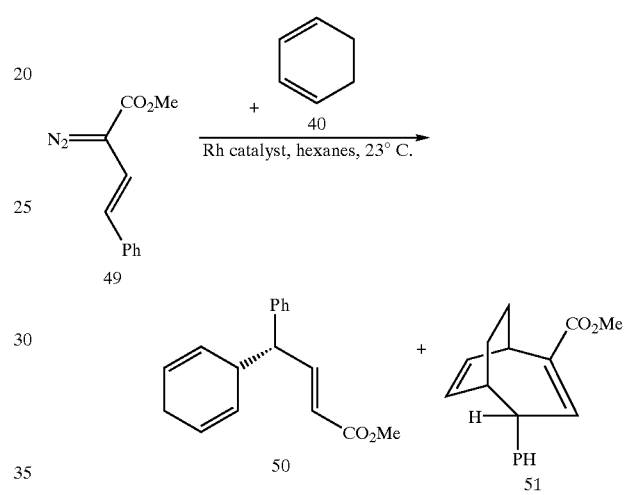

The catalyst has a major effect on the product distribution in this reaction, as shown in Table VII, below:

TABLE VII

| Rh catalyst | 50:51 |
|---|---|
| $Rh_2(S\text{-}DOSP)_4$ | 86:14 |
| $Rh_2(OOct)_4$ | 26:74 |
| $Rh_2(OPiv)_4$ | 19:81 |
| $Rh_2(TFA)_4$ | 46:54 |
| $Rh_2(TPA)_4$ | 30:70 |

In Table VII, $Rh_2(OOct)_4$ represents dirhodium(II) tetraoctanoate, $Rh_2(OPiv)_4$ represents dirhodium(II) tetra (trimethylacetate), $Rh_2(TFA)_4$ represents dirhodium(II) tetra(trifluoroacetate), and $Rh_2(TPA)_4$ represents dirhodium (II) tetra(triphenylacetate). For example, when $Rh_2(OOct)_4$ is used as catalyst, cyclopropanation becomes the preferred reaction. From the range of catalysts that were studied, it appears that catalyst exhibits a subtle combination of steric and electronic effects. At present, $Rh_2(S\text{-}DOSP)_4$ is the best catalyst for limiting the cyclopropanation reaction, resulting in a 84:16 ratio of 50:51.

One possible mechanism for the formation of cyclohexadiene 50 would be an allylic C—H insertion between 49 and 1,3-cyclohexadiene 40 to form 52 which could then undergo a Cope rearrangement to form 50, as shown in Scheme XIV, below:

SCHEME XIV

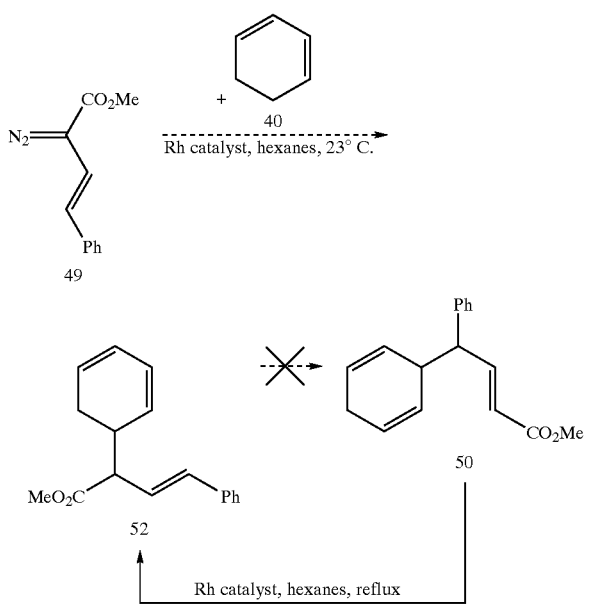

However, there is no apparent driving force for the Cope rearrangement of 50 and 52. Indeed, there is evidence that the driving force for the Cope rearrangement is in the reverse direction by heating 50 in refluxing hexane, because, under these conditions, 50 slowly rearranges to 52. In view of this, alternative mechanistic possibilities need to be considered. It is conceivable that 50 is derived by an intercepted C—H insertion process or by means of an ene reaction where the vinylcarbenoid reacts as a 2n system.

The reaction described in Scheme XIII was extended to a range of arylvinyldiazoacetates, as illustrated in Scheme XV and Table IX, below:

SCHEME XV

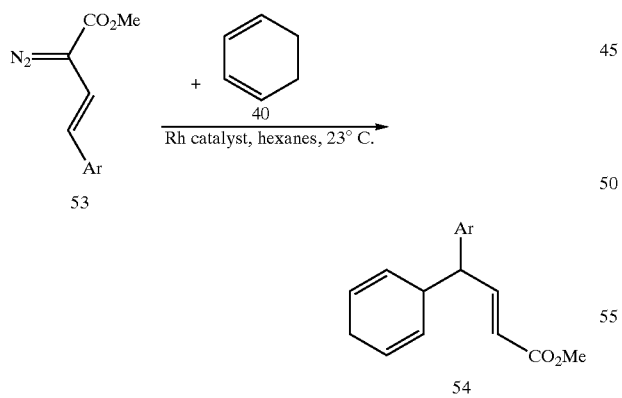

TABLE IX

| | Ar | yield 54, % | ee 54, % |
|---|---|---|---|
| a | p-MeO-Ph | 58 | 99 |
| b | 3,4-diClPh | 59 | 99 |
| c | 2-naphthyl | 50 | 99 |

TABLE IX-continued

| | Ar | yield 54, % | ee 54, % |
|---|---|---|---|
| d | o-MeO-Ph | 17 | 86 |
| e | 1-naphthyl | 22 | 84 |

Each of the reactions was performed using the following general procedure, which is illustrated using methyl 3,4-dichlorophenylvinyldiazoacetate 53b as a reactant. A solution of the vinyldiazoacetate 53b (207 mg, 0.764 mmol) in dry hexanes (20 ml) was added dropwise over 15 minutes to a flame-dried flask containing a stirred solution of $Rh_2(S\text{-}DOSP)_4$ (12 mg, $6.4\times10^{-3}$ mmol) and the diene (0.4 ml, 4 mmol) in dry hexane (30 ml) at room temperature. After 16 hours, the solvent was removed under reduced pressure. Purification by flash silica gel column chromatography (petroleum ether/ether, 9:1, $R_f$=0.24) gave 54b in 59% yield as a clear oil. 99% ee (determined by HPLC: Daicel-OD, 0.8% i-Pr-OH in hexanes, 0.8 ml/min; Tr=12.06 min (minor), 23.73 min (major)). $[\alpha]^{25}_D$=+4° (c 2.0 8, $CHCl_3$). IR (neat) 3029, 2954, 2863, 2817, 1726, 1651 $cm^{-1}$; $^1H$ NMR (300 MHz) δ7.36 (d, 1 H, J=8.0 Hz), 7.27 (d, 1H, J=2.5 Hz), 7.10 (dd, 1H, J=15.5 Hz), 7.02 (dd, 1H , J=8.0, 2.5 Hz), 5.81 (d, 1H, 15.5 Hz), 5.75 (Br. d, 2H, J=12.0 Hz), 5.57 (Br. d, 1H, J=10.0 Hz), 5,43 (Br. d, 1H, J=10.0 Hz), 3.71 (s, 3H) , 3.38 (dd, 1H, J=8.5, 8.0 Hz), 3.17–3.15 (m, 1H) 2.62–2.48 (m, 2H); $^{13}C$ NMR (125 MHz) δ166.5, 148.1, 140.7, 132.4, 130.8, 130.4, 130.2, 127.6, 126.83, 126.79, 125.7, 125.3, 122.9, 53.6, 51.6, 40,1, 26.3. HRMS calcd for $C_{17}H_{16}O_2Cl_2$, 322.0527, found, 322.0504.

The reactions with m- or p-substituted benzene (53a, 53b) or 2-naphthyl derivatives (53c) result in the formation of 54a–54c with exceptionally high levels of asymmetric induction (99% ee). In contrast, the reaction with o-substituted benzene (53d) and 1-naphthyl (53e) result in the formation of 54d and 54e with lower enantioselectivity (84–86% ee). Also, the yields of 54d and 54e were greatly decreased compared to 54a–54c, because, it is believed, the major product in these last two reactions was the cyclopropanation/Cope rearrangement product, analogous to 51.

The cyclohexadiene 54b is an excellent precursor for the formal synthesis of (−)-sertraline, as illustrated in Scheme XVI, below:

SCHEME XVI

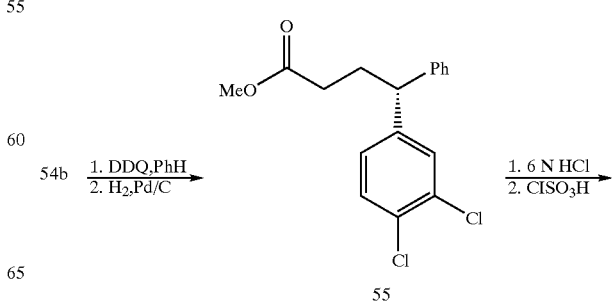

-continued

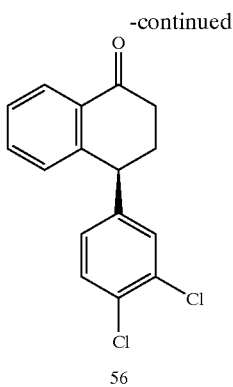

56

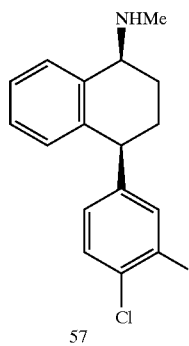

57

Oxidation of 54b with DDQ followed by catalytic hydrogenation over Pd/C formed the 4,4-diarylbutanoate 55 (52% yield for 3 steps from 53b) with minimal racemization (96% ee). Ester hydrolysis of the 4,4-diarylbutanoate 55 followed by an intramolecular Freidel-Crafts acylation generated the tetralone 56 in 79% yield for 2 steps. Conversion of the tetralone 56 to (−)-sertraline 57 was carried out following the method described in Corey, which is hereby incorporated by reference.

The general chemistry described in this example is applicable to other vinylcarbenoid systems as illustrated in Scheme XVII, below:

SCHEME XVII

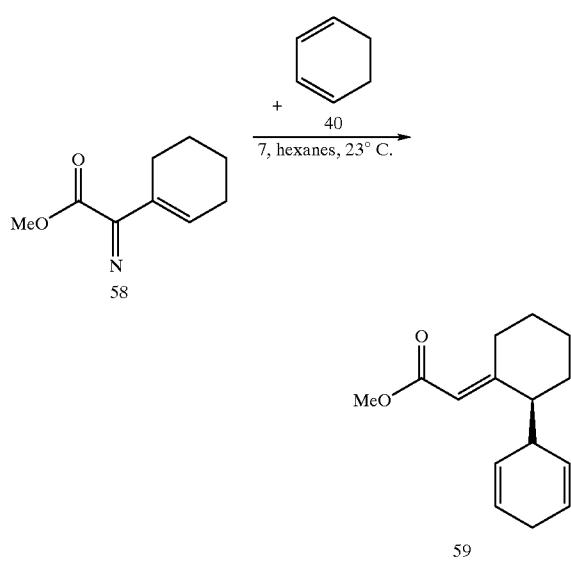

-continued

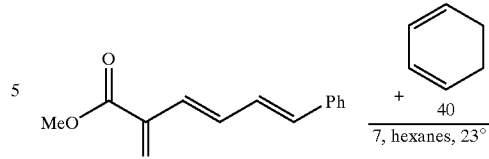

60

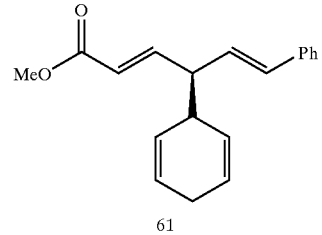

61

Rh$_2$(S-DOSP)$_4$-catalyzed decomposition of the cyclic vinyldiazoacetate 58 in the presence of 1,3-cyclohexadiene 40 resulted in the formation of the 1,4-cyclohexadiene 59 in 73% yield and 97% ee. The absolute configuration of compound 59 was determined by DDQ oxidation and ozonolysis to afford the 2-phenylcyclohexanone in a 56% yield. Found $[\alpha]^{26}_D = -17$ (c=1.66, PhH). Lit. value: $[\alpha]^{24}_D = -113.5$ (c=0.60, PhH), S-isomer. (Berti et al., J. Chem. Soc., pp. 3371–3377 (1971), which is hereby incorporated by reference.) Similarly, decomposition of the dienyldiazoacetate 60 in the presence of 1,3-cyclohexadiene 40 resulted in the formation of 61 (60% yield and 99% ee), in which both diene components have moved out of conjugation.

Although the invention has been described in detail for the purpose of illustration, it is understood that such detail is solely for that purpose, and variations can be made therein by those skilled in the art without departing from the spirit and scope of the invention which is defined by the claims which are set forth below.

What is claimed is:

1. A compound having the formula:

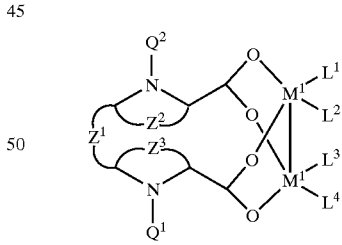

wherein $M^1$ and $M^2$ are the same or different and are transition metal atoms or ions; $Z^2$ and $Z^3$, independently, are the atoms necessary to complete a 3–12 membered heterocyclic ring; $Z^1$ is an alkylene or arylene group; $Q^1$ and $Q^2$ are the same or different and are electron withdrawing groups; $L^1$ and $L^3$, taken together, represent —O—CR$^{13}$—O—; $L^2$ and $L^4$, taken together, represent —O—CR$^{14}$—C—; and $R^{13}$ and $R^{14}$ are the same or different and are selected from the group consisting of alkyl groups and aryl groups or $R^{13}$ and $R^{14}$ represent alkylene or arylene groups that are directly or indirectly bonded to one another.

2. A compound according to claim 1, having the formula:

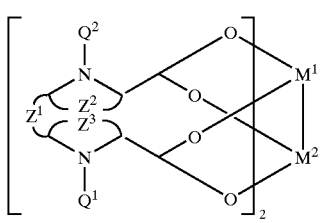

3. A compound according to claim 1, wherein $M^1$ and $M^2$ are independently selected from Rh, Ru, Mo, Pd, and Re.

4. A compound according to claim 1, wherein each of $M^1$ and $M^2$ is Rh.

5. A compound according to claim 1, wherein $Q^1$ is selected from the group of moieties having the formulae —C(O)R$^1$, —SO$_2$R$^1$, and —P(O)R$^1$R$^{1'}$; wherein $Q^2$ is selected from the group of moieties having the formulae —C(O)R$^2$, —SO$_2$R$^2$, and —P(O)R$^2$R$^{2'}$; and wherein each of R$^1$, R$^{1'}$, R$^2$, and R$^{2'}$ is independently selected from an alkyl group, an aryl group, and an alkoxy group.

6. A compound according to claim 5, wherein $Q^1$ has the formula —SO$_2$R$^1$; $Q^2$ has the formula —SO$_2$R$^2$; and R$^1$ and R$^2$ are the same or different and are alkyl or aryl groups.

7. A compound according to claim 6, wherein each of R$^1$ and R$^2$ is independently selected from the group consisting of 4-(t-butyl)phenyl, 2,4,6-trimethylphenyl, and 2,4,6-triisopropylphenyl.

8. A compound according to claim 1, wherein $Z^2$ and $Z^3$ each have the formula —CH$_2$CH$_2$—.

9. A compound according to claim 1, wherein $Z^1$ is 1,3-phenylene.

10. A compound according to claim 1 having one of the following formulae:

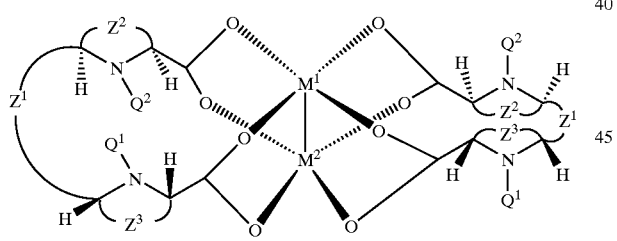

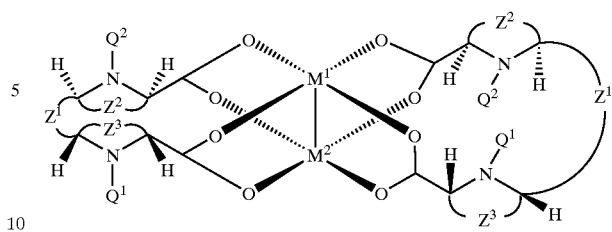

11. A compound according to claim 1 having one of the following formulae:

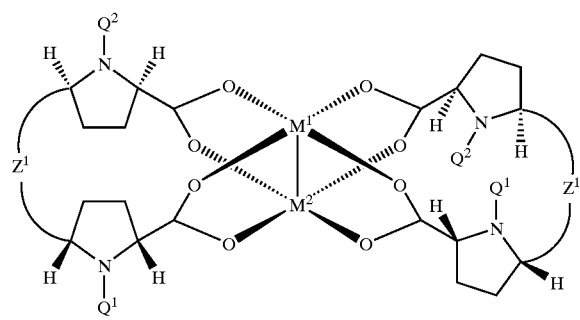

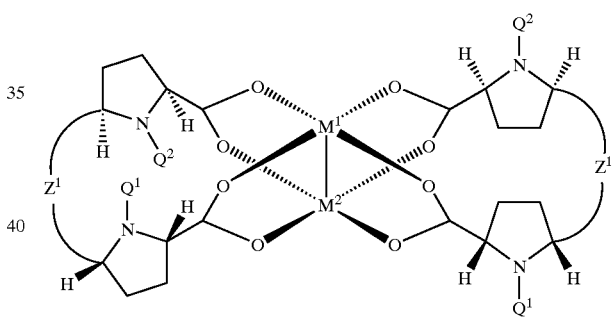

12. A compound according to claim 1 having one of the following formulae:

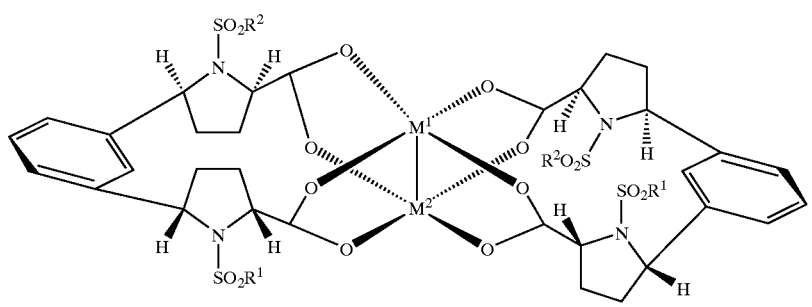

-continued

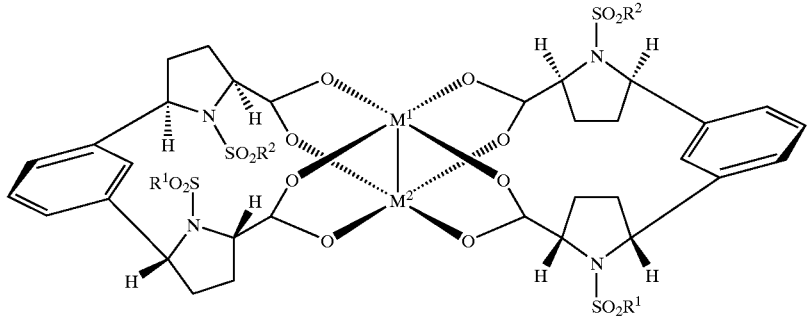

wherein $R^1$ and $R^2$ are the same or different and are alkyl or aryl groups.

13. A compound comprising:

a first metal atom and a second metal atom bonded to one another along an axis and two carboxylate ligands wherein each of said two carboxylate ligands comprises two carboxylate groups bonded to each other via a moiety having the formula:

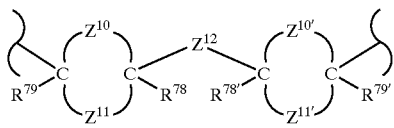

wherein $Z^{10}$ and $Z^{11}$, together with the atoms to which they are bonded form a 3–12 membered ring; wherein $Z^{10'}$ and $Z^{11'}$, together with the atoms to which they are bonded form a 3–12 membered ring; wherein $R^{78}$, $R^{78'}$, $R^{79}$, and $R^{79'}$ are independently selected from the group consisting of H, an alkyl group, and an aryl group; wherein $Z^{12}$ is an alkylene or arylene group; wherein each of said two carboxylate groups comprises a first carboxylate oxygen atom ("$O^1$"), a second carboxylate oxygen atom ("$O^2$"), and a carbon ("C") to which said $O^1$ and said $O^2$ are bonded thereby forming two $O^1$—C—$O^2$ moieties, each $O^1$—C—$O^2$ moiety defining a plane which is substantially parallel to said axis; wherein said $O^1$ of each of said two carboxylate groups of each of said two carboxylate ligands is bonded to said first metal atom; wherein said $O^2$ of each of said two carboxylate groups of each of said two carboxylate ligands is bonded to said second metal atom; wherein each of said two carboxylate ligands further comprises at least two chiral centers; and wherein said compound has $D_2$ symmetry.

14. A compound according to claim 13, wherein none of $Z^{10}$, $Z^{10'}$, $Z^{11}$, and $Z^{11'}$ represents a direct bond between the carbon atoms to which they are bonded.

15. A compound according to claim 14, wherein at least one of $Z^{10}$ and $Z^{10'}$ has the formula —NQ—, at least one of $Z^{11}$ and $Z^{11'}$ is an arylene or alkylene group, and Q is an electron withdrawing group.

16. A method for making a compound having the formula:

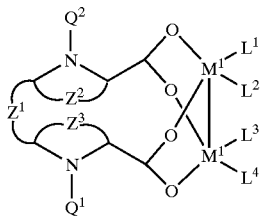

wherein $M^1$ and $M^2$ are the same or different and are transition metal atoms or ions; $Z^2$ and $Z^3$, independently, are the atoms necessary to complete a 3–12 membered heterocyclic ring; $Z^1$ is an alkylene or arylene group; and $Q^1$ and $Q^2$ are the same or different and are electron withdrawing groups; $L^1$ and $L^3$, taken together, represent —O—CHR$^{13}$—O—; $L^2$ and $L^4$, taken together, represent —O—CHR$^{14}$—O—; and $R^{13}$ and $R^{14}$ are the same or different and are selected from the group consisting of alkyl groups and aryl groups or $R^{13}$ and $R^{14}$ represent alkylene or arylene groups that are directly or indirectly bonded to one another, said method comprising:

providing a ligand having the formula:

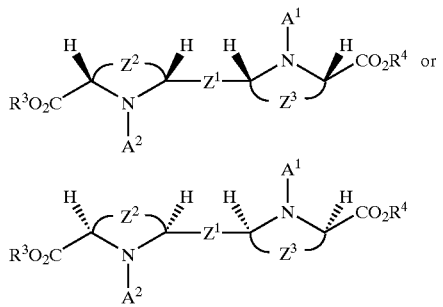

or a mixture thereof, wherein each of $A^1$ and $A^2$ is independently selected from the group consisting of a hydrogen atom and an electron withdrawing group and each of $R^3$ and $R^4$ is independently selected from the group consisting of H, alkyl, and aryl; and converting the ligand with a bis-metal salt under conditions effective to produce the compound.

17. A method according to claim 16, wherein $Z^2$ and $Z^3$ each have the formula —CH$_2$CH$_2$—; each of $M^1$ and $M^2$ is Rh; $Z^1$ is 1,3-phenylene; $Q^1$ is selected from the group of moieties having the formulae —C(O)R$^1$, —SO$_2$R$^1$, and —P(O)R$^1$R$^{1'}$; $Q^2$ is selected from the group of moieties having the formulae —C(O)R$^2$, —SO$_2$R$^2$, and —P(O)R$^2$R$^{2'}$;

and each of $R^1$, $R^{1'}$, $R^2$, and $R^{2'}$ is an alkyl group, an aryl group, or an alkoxy group.

18. A method according to claim 16, wherein the bis-metal salt has the formula $M^1M^2(OOR^5)_4$, wherein $R^5$ is an alkyl group or an aryl group.

19. A method according to claim 16, wherein each of $M^1$ and $M^2$ is Rh and the bis-metal salt is $Rh_2(OOCH_3)_4$.

20. A compound having one of the following formulae:

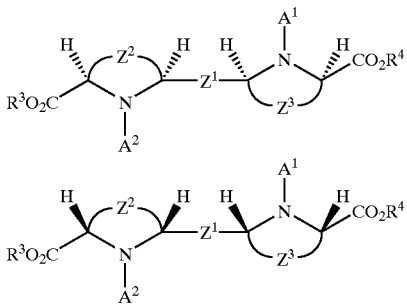

wherein $Z^2$ and $Z^3$, independently, are the atoms necessary to complete a 3–12 membered heterocyclic ring; $Z^1$ is an alkylene or arylene group; $A^1$ and $A^2$ are independently selected from the group consisting of a hydrogen atom and an electron withdrawing group; and each each of $R^3$ and $R^4$ is independently selected from the group consisting of H, alkyl, and aryl.

21. A method for preparing an N-substituted compound having the formula:

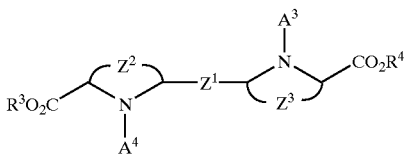

wherein $Z^2$ and $Z^3$, independently, are the atoms necessary to complete a 3–12 membered heterocyclic ring; $Z^1$ is an alkylene or arylene group; $A^3$ and $A^4$ are the same or different and are electron withdrawing groups having the formulae —C(O)$R^2$, —SO$_2R^2$, or —P(O)$R^2R^{2'}$; each of $R^1$, $R^{1'}$, $R^2$, and $R^{2'}$ is an alkyl group, an aryl group, or an alkoxy group; and each of $R^3$ and $R^4$ is independently selected from the group consisting of H, alkyl, and aryl, said method comprising:

providing an N-unsubstituted compound having the formula:

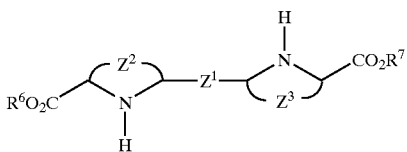

wherein $R^6$ and $R^7$ is independently selected from an alkyl group or an aryl group; and converting the N-unsubstituted compound to the N-substituted compound with an acylating agent, a sulfonylating agent, or a phosphonylating agent.

22. A method for preparing an N-unsubstituted compound having the formula:

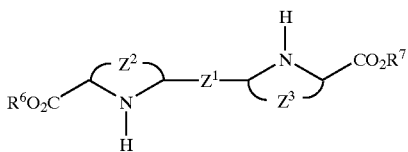

wherein $Z^2$ and $Z^3$, independently, are the atoms necessary to complete a 3–12 membered heterocyclic ring; $Z^1$ is an alkylene or arylene group; and $R^6$ and $R^7$ is independently selected from an alkyl group or an aryl group, said method comprising:

providing an unsaturated heterocyclic compound having the formula:

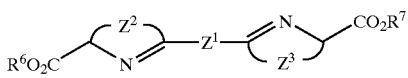

and converting the unsaturated heterocyclic compound to the N-unsubstituted compound using hydrogenation.

23. A compound having one of the following formulae:

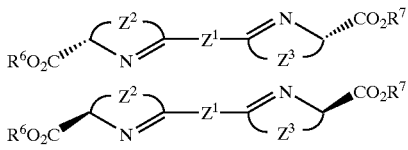

wherein $Z^2$ and $Z^3$, independently, are the atoms necessary to complete a 3–12 membered heterocyclic ring; $Z^1$ is an alkylene or arylene group; and $R^6$ and $R^7$ is independently selected from an alkyl group or an aryl group.

24. A compound according to claim 23, wherein $Z^1$ is a 1,3-phenylene group.

25. A method for preparing an unsaturated heterocyclic compound having the formula:

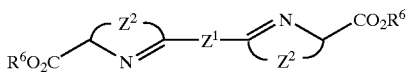

wherein $Z^2$ represents the atoms necessary to complete a 3–12 membered heterocyclic ring; $Z^1$ is an alkylene or arylene group; and $R^6$ is selected from an alkyl group or an aryl group, said method comprising:

providing a cyclic ketone having the formula:

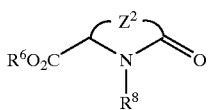

wherein $R^8$ is an amine-protecting group; and converting the cyclic ketone to the N-unsaturated heterocyclic compound with a bis-lithium compound having the formula $Z^1Li_2$.

26. A method according to claim 25, wherein the bis-lithium compound is 1,3-dilithiobenzene.

27. A method according to claim 25, wherein the N-unsaturated heterocyclic compound has the formula:

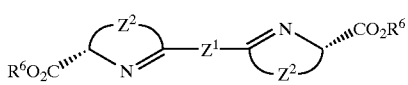

and the cyclic ketone has the formula:

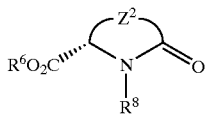

or wherein the N-unsaturated heterocyclic compound has the formula:

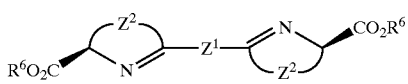

and the cyclic ketone has the formula:

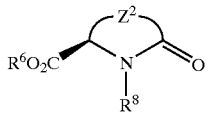

28. A method of producing a compound having the formula:

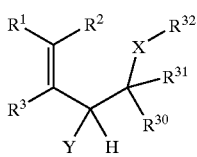

where $R^1$, $R^2$, and $R^3$ are independently selected from H, alkyl, aryl, or vinyl or where $R^1$ and $R^3$, together with the atoms to which they are bonded, form a 5–12 membered ring; Y is an electron withdrawing group; X is $NR^{11}$; $R^{31}$ and $R^{32}$, taken together with the atoms to which they are bonded, form a ring having the formula:

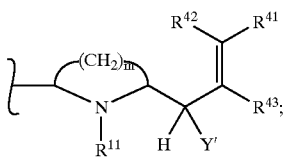

$R^{41}$, $R^{42}$, and $R^{43}$ are independently selected from H, alkyl, aryl, or vinyl or $R^{41}$ and $R^{43}$, together with the atoms to which they are bonded, form a 5–12 membered ring; Y' is an electron withdrawing group; m is 2–9; $R^{11}$ is H, an alkyl group, an aryl group, an acyl group, an alkoxycarbonyl group, or a silyl group having the formula —$SiR^{33}R^{34}R^{35}$; $R^{30}$ is selected from the group consisting of H, alkyl, aryl, and vinyl; and $R^{33}$, $R^{34}$, and $R^{35}$ are independently selected from an alkyl group and an aryl group; said method comprising:

providing a diazo compound having the formula:

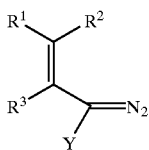

and converting the diazo compound with a cyclic amine having the formula:

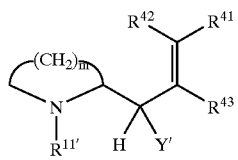

in the presence of a bis-transition metal catalyst and under conditions effective to produce the compound.

29. A method according to claim 28, wherein the compound has the formula:

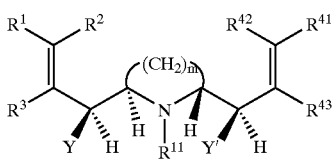

30. A method of producing a compound having the formula:

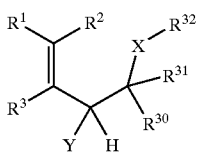

wherein $R^1$, $R^2$, and $R^3$ are independently selected from H, alkyl, aryl, or vinyl or where $R^1$ and $R^3$, together with the atoms to which they are bonded, form a 5–12 membered ring; Y is an electron withdrawing group; X is $CH_2$, O, or $NR^{11}$; $R^{11}$ is H, an alkyl group, an aryl group, an acyl group, an alkoxycarbonyl group, or a silyl group having the formula —$SiR^{33}R^{34}R^{35}$; each of $R^{30}$ and $R^{31}$ is independently selected from the group consisting of H, alkyl, aryl, and vinyl; $R^{32}$ is an alkyl group, an aryl group, an acyl group, an alkoxycarbonyl group, or a silyl group having the formula —$SiR^{36}R^{37}R^{38}$; and $R^{33}$, $R^{34}$, $R^{35}$, $R^{36}$, $R^{37}$, and $R^{38}$ are independently selected from an alkyl group and an aryl group; provided that when each of $R^{30}$ and $R^{31}$ is H, X is not $CH_2$, said method comprising:

providing a diazo compound having the formula:

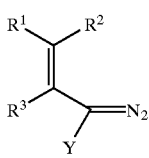

and converting the diazo compound with a material having the formula:

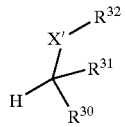

in the presence of a bis-transition metal catalyst and under conditions effective to produce the compound, wherein X' is $CH_2$, O or $NR^{11'}$; $R^{11'}$ is an alkyl group, an aryl group, an acyl group, an alkoxycarbonyl group, or a silyl group having the formula —$SiR^{36}R^{37}R^{38}$; and $R^{33}$, $R^{34}$, and $R^{35}$ are independently selected from an alkyl group and an aryl group.

31. A method according to claim 30, wherein X is O, $R^{32}$ is a trialkylsilyl group or a triarylsilyl group, and $R^{31}$ is H.

32. A method according to claim 30, wherein X is $NR^{11}$, $R^{11}$ is am alkyl group, and $R^{32}$ is selected from an acyl group and an alkoxycarbonyl group.

33. A method according to claim 30, wherein $R^1$ and $R^3$ are independently selected from H, alkyl, aryl, or vinyl.

34. A method according to claim 30, wherein $R^1$ and $R^3$, together with the atoms to which they are bonded, from a 5–12 membered ring.

* * * * *